(12) United States Patent
Shubinsky et al.

(10) Patent No.: US 12,076,531 B2
(45) Date of Patent: *Sep. 3, 2024

(54) ACOUSTIC FLOW SENSOR FOR CONTINUOUS MEDICATION FLOW MEASUREMENTS AND FEEDBACK CONTROL OF INFUSION

(71) Applicant: ICU Medical, Inc., San Clemente, CA (US)

(72) Inventors: Gary David Shubinsky, San Clemente, CA (US); Jeffrey Donald Merwin, San Clemente, CA (US); Tamas R. Ban, San Clemente, CA (US); Ion Vergil Nicolaescu, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,221

(22) Filed: May 5, 2022

(65) Prior Publication Data

US 2022/0331518 A1 Oct. 20, 2022

Related U.S. Application Data

(63) Continuation of application No. 16/308,425, filed as application No. PCT/US2017/036619 on Jun. 8, 2017, now Pat. No. 11,324,888.

(Continued)

(51) Int. Cl.
*A61M 5/172* (2006.01)
*A61M 5/142* (2006.01)

(52) U.S. Cl.
CPC ........ *A61M 5/172* (2013.01); *A61M 5/14212* (2013.01); *A61M 2205/3334* (2013.01); *A61M 2205/3375* (2013.01); *A61M 2205/52* (2013.01)

(58) Field of Classification Search
CPC .............. A61M 5/172; A61M 5/14212; A61M 2205/3334; A61M 2205/3375; A61M 2205/52

(Continued)

(56) References Cited

U.S. PATENT DOCUMENTS 3,401,337 A 9/1968 Beusman et al.
3,484,681 A 12/1969 Grady, Jr. et al.

(Continued)

FOREIGN PATENT DOCUMENTS

AU 2013216679 9/2013
BR PI0704229-9 11/2009

(Continued)

OTHER PUBLICATIONS

Abbott Laboratories, "LifeCare® 5000, Plum®: Concurrent Flow Infusion System with DataPort™", System Operating Manual, Version 1.6, Jul. 1998, pp. 76.

(Continued)

*Primary Examiner* — Michael J Tsai
*Assistant Examiner* — Nidah Hussain
(74) *Attorney, Agent, or Firm* — Knobbe, Martens, Olson, & Bar, LLP

(57) ABSTRACT

An infusion system determines a volumetric flow rate of infusion fluid delivered by an infusion pump along a flow path based on: an upstream acoustic signal emitted by at least one upstream acoustic sensor and detected by at least one downstream acoustic sensor; a downstream acoustic signal emitted by the downstream acoustic signal and detected by the upstream acoustic sensor; and a phase delay between the upstream acoustic signal and the downstream acoustic signal either upstream or downstream. The infusion system automatically adjusts the infusion pump based on the (Continued)

determined volumetric flow rate to achieve a desired volumetric flow rate of the infusion fluid along the flow path.

13 Claims, 13 Drawing Sheets

Related U.S. Application Data

(60) Provisional application No. 62/348,301, filed on Jun. 10, 2016.

(58) Field of Classification Search
USPC .......................................................... 604/506
See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,057,228 A | 11/1977 | Völker et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |

(56) References Cited

U.S. PATENT DOCUMENTS

| | | |
|---|---|---|
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,040,699 A | 8/1991 | Gangemi |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |

(56) References Cited

U.S. PATENT DOCUMENTS

| | | |
|---|---|---|
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |

(56) References Cited

U.S. PATENT DOCUMENTS

| | | |
|---|---|---|
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,066 A * | 8/1999 | Harris .............. A61B 8/06 600/436 |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |

(56) References Cited

U.S. PATENT DOCUMENTS

| | | |
|---|---|---|
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,336,053 B1 | 1/2002 | Beatty |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |

(56) References Cited

U.S. PATENT DOCUMENTS

| | | |
|---|---|---|
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |

(56) References Cited

U.S. PATENT DOCUMENTS

| | | |
|---|---|---|
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Gimdt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,477,997 B2 | 1/2009 | Kaplit |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,976,508 B2 | 7/2011 | Hoag |
| 7,981,073 B2 | 7/2011 | Mollstam |
| 7,981,082 B2 | 7/2011 | Wang et al. |
| 7,998,134 B2 | 8/2011 | Fangrow |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,197,444 B1 | 6/2012 | Bazargan et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,409,164 B2 | 4/2013 | Fangrow |
| 8,449,524 B2 | 5/2013 | Braig et al. |
| 8,469,942 B2 | 6/2013 | Kow et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,728,020 B2 | 5/2014 | Caleffi et al. |
| 8,758,306 B2 | 6/2014 | Lopez et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |

(56) References Cited

U.S. PATENT DOCUMENTS

| | | |
|---|---|---|
| 9,190,010 B2 | 11/2015 | Vik et al. |
| 9,240,002 B2 | 1/2016 | Hume et al. |
| 9,272,089 B2 | 3/2016 | Jacobson et al. |
| 9,316,216 B1 | 4/2016 | Cook et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,545,475 B2 | 1/2017 | Borges et al. |
| 9,707,341 B2 | 7/2017 | Dumas et al. |
| 9,764,087 B2 | 9/2017 | Peterfreund et al. |
| 9,852,265 B1 | 12/2017 | Treacy et al. |
| 9,883,987 B2 | 2/2018 | Lopez et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,099,009 B1 | 10/2018 | Anderson et al. |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,709,885 B2 | 7/2020 | Janders et al. |
| 10,850,024 B2 | 12/2020 | Day et al. |
| 10,874,793 B2 | 12/2020 | Oruklu et al. |
| 11,004,035 B2 | 5/2021 | Hume et al. |
| D923,050 S | 6/2021 | Kataoka et al. |
| 11,029,911 B2 | 6/2021 | Fryman |
| D928,813 S | 8/2021 | Nurutdinov et al. |
| D928,840 S | 8/2021 | Amit et al. |
| 11,090,431 B2 | 8/2021 | Dumas, III et al. |
| D931,884 S | 9/2021 | Bryant et al. |
| 11,135,360 B1 | 10/2021 | Jacobson et al. |
| 11,246,985 B2 | 2/2022 | Gylland et al. |
| 11,278,671 B2 | 3/2022 | Cavendish, Jr. et al. |
| 11,298,456 B2 | 4/2022 | Shubinsky et al. |
| 11,324,888 B2 * | 5/2022 | Shubinsky ........ A61M 5/14212 |
| 11,344,668 B2 | 5/2022 | Sileika et al. |
| 11,344,673 B2 | 5/2022 | Lindo et al. |
| 11,376,361 B2 | 7/2022 | Ruchti et al. |
| 11,378,430 B2 | 7/2022 | Ruchti et al. |
| 11,395,875 B2 | 7/2022 | Rubalcaba, Jr. et al. |
| 11,433,177 B2 | 9/2022 | Oruklu et al. |
| 11,596,737 B2 | 3/2023 | Dumas, III et al. |
| 11,599,854 B2 | 3/2023 | Hume et al. |
| 11,623,042 B2 | 4/2023 | Day |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0093641 A1 | 7/2002 | Ortyn et al. |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0133166 A1 | 7/2004 | Moberg et al. |
| 2004/0145114 A1 | 7/2004 | Ippolito et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |

(56) References Cited

U.S. PATENT DOCUMENTS

| | | |
|---|---|---|
| 2004/0172283 A1 | 9/2004 | Vanderveen |
| 2004/0172289 A1 | 9/2004 | Kozic et al. |
| 2004/0172301 A1 | 9/2004 | Mihai et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084286 A1 | 4/2007 | Ajay et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1 | 7/2007 | McGillin et al. |
| 2007/0179436 A1 | 8/2007 | Braig et al. |
| 2007/0180916 A1 | 8/2007 | Tian et al. |
| 2007/0191770 A1 | 8/2007 | Moberg et al. |
| 2007/0191817 A1 | 8/2007 | Martin |
| 2007/0197963 A1 | 8/2007 | Griffiths et al. |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |

(56) References Cited

U.S. PATENT DOCUMENTS

| | | |
|---|---|---|
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0198347 A1 | 8/2009 | Kirzinger |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0280430 A1 | 11/2010 | Caleffi et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1* | 6/2011 | DelCastillo ....... A61M 5/16831 604/67 |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0264006 A1 | 10/2011 | Ali et al. |
| 2011/0264043 A1 | 10/2011 | Kotnick et al. |
| 2011/0282321 A1 | 11/2011 | Steil et al. |

(56) References Cited

U.S. PATENT DOCUMENTS

| | | |
|---|---|---|
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0025995 A1 | 2/2012 | Moberg et al. |
| 2012/0035535 A1* | 2/2012 | Johnson .................. G01F 1/74 |
| | | 604/67 |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0089411 A1 | 4/2012 | Srnka et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0218080 A1 | 8/2013 | Peterfreund et al. |
| 2013/0116649 A1 | 9/2013 | Kouyoumjian et al. |
| 2013/0253430 A1 | 9/2013 | Kouyoumjian et al. |
| 2013/0253946 A1 | 9/2013 | Broselow |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0322201 A1 | 12/2013 | Hitchcock et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0267563 A1 | 9/2014 | Baca et al. |
| 2014/0303754 A1 | 10/2014 | Nixon et al. |
| 2014/0350513 A1 | 11/2014 | Oruklu et al. |
| 2015/0025453 A1 | 1/2015 | Ledford et al. |
| 2015/0033073 A1 | 1/2015 | Yang et al. |
| 2015/0065988 A1 | 3/2015 | Holderle et al. |
| 2015/0168958 A1 | 6/2015 | Downie et al. |
| 2015/0224252 A1 | 8/2015 | Borges et al. |
| 2015/0265765 A1 | 9/2015 | Yavorsky et al. |
| 2015/0338340 A1 | 11/2015 | Jiang et al. |
| 2015/0343141 A1 | 12/2015 | Lindo et al. |
| 2015/0371004 A1 | 12/2015 | Jones |
| 2016/0042264 A1 | 2/2016 | Borges et al. |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1* | 6/2016 | Biasi .................. F04B 53/08 |
| | | 417/279 |
| 2016/0175517 A1 | 6/2016 | Sileika et al. |
| 2016/0193604 A1 | 7/2016 | McFarland et al. |
| 2016/0253460 A1 | 9/2016 | Kanada |
| 2016/0256622 A1 | 9/2016 | Day et al. |
| 2016/0339167 A1 | 11/2016 | Ledford et al. |
| 2017/0043089 A1 | 2/2017 | Handler |
| 2017/0132867 A1 | 5/2017 | Berg et al. |
| 2017/0354941 A1 | 12/2017 | Brown et al. |
| 2018/0018440 A1 | 1/2018 | Sugawara |
| 2018/0028749 A1 | 2/2018 | Dumas, III et al. |
| 2018/0300994 A1 | 10/2018 | Nelson et al. |
| 2019/0091401 A1 | 3/2019 | Ruchti et al. |
| 2019/0101425 A1* | 4/2019 | Ruchti .................. G01F 1/74 |
| 2019/0117890 A1 | 4/2019 | Oruklu et al. |
| 2019/0196770 A1 | 6/2019 | Fryman |
| 2019/0282757 A1 | 9/2019 | Gylland et al. |
| 2020/0113784 A1 | 4/2020 | Lopez et al. |
| 2021/0260283 A1 | 8/2021 | Oruklu et al. |
| 2021/0397396 A1 | 12/2021 | Fryman |
| 2022/0142865 A1 | 5/2022 | Janssen |
| 2022/0176037 A1 | 6/2022 | Jacobson et al. |
| 2022/0184302 A1 | 6/2022 | Cavendish, Jr. et al. |
| 2022/0296806 A1 | 9/2022 | Shubinsky et al. |
| 2022/0305200 A1 | 9/2022 | Gylland et al. |
| 2022/0362463 A1 | 11/2022 | Lindo et al. |
| 2023/0010290 A1 | 1/2023 | Oruklu et al. |
| 2023/0010638 A1 | 1/2023 | Rubalcaba, Jr. et al. |
| 2023/0017117 A1 | 1/2023 | Sileika et al. |
| 2023/0058662 A1 | 2/2023 | Ruchti et al. |
| 2023/0058894 A1 | 2/2023 | Ruchti et al. |

FOREIGN PATENT DOCUMENTS

| | | |
|---|---|---|
| CA | 2 113 473 | 3/1993 |
| CA | 2 551 817 | 7/2005 |
| CN | 107106042 | 8/2017 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |

(56) References Cited

FOREIGN PATENT DOCUMENTS

| | | |
|---|---|---|
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2017/051271 | 3/2017 |
| WO | WO 2017/144366 | 8/2017 |
| WO | WO 2017/197024 | 11/2017 |
| WO | WO 2017/214441 | 12/2017 |
| WO | WO 2019/092680 | 5/2019 |
| WO | WO 2020/214717 | 10/2020 |
| WO | WO 2022/020184 | 1/2022 |
| WO | WO 2022/125471 | 6/2022 |
| WO | WO 2023/064662 | 4/2023 |

OTHER PUBLICATIONS

Daimiwal et al., "Wireless Transfusion Supervision and Analysis Using Embedded System", IEEE, 2010 International Conference ICBBT, China, Apr. 2010, pp. 56-60.
International Search Report and Written Opinion received in PCT Application No. PCT/US2017/036619, dated Aug. 21, 2017 in 16 pages.
International Preliminary Report on Patentability and Written Opinion received in PCT Application No. PCT/US2017/036619, dated Dec. 20, 2018 in 14 pages.
Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

(56) References Cited

OTHER PUBLICATIONS

Alaris® Medical Systems, "Signature Edition® Gold—Single & Dual Channel Infusion System", San Diego, CA, USA, date unknown, but believed to be at least as early as Nov. 29, 2008, pp. 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About BloodGlucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. <http://web.archive.org/web/20160403140025/http://www.baxter.com/news-media/newsroom/press-releases/2014/05_08_14_sigma.page>.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, <https://store.cerner.com/items/7>.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously",<https://web.archive.org/web/20090813092423/http://www.diffen.com/difference/Continually_vs_Continuously>, as accessed Aug. 13, 2009 in 4 pages.
"CritiCore® Monitor: Critical Fluid Output and Core Bladder Temperature Monitor", Bard Urological Catheter Systems, Advertisement, 2005, pp. 2.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. <http://archive.epo.org/epo/pubs/oj013/11_13/11_5033.pdf>.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. <http://archive.epo.org/epo/pubs/oj009/12_09/12_5829.pdf>.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.

Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", <http://www.merriam-webster.com/dictionary/froth>, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. <www.hospira.com/products_and_services/infusion_pumps/plum/index>.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator",Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", <https://www.elektronik.ropla.eu/pdf/stock/mcp/mta11200b.pdf>, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

(56) References Cited

OTHER PUBLICATIONS

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

SGS-Thomson Microelectronics, "L6219—Stepper Motor Drive", Datasheet, Dec. 1996, pp. 10.

SGS-Thomson Microelectronics, "PBL3717A—Stepper Motor Drive", Datasheet, Apr. 1993, pp. 11.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Smith, Joe, "Infusion Pump Informatics", CatalyzeCare: Transforming Healthcare, as printed May 12, 2011, pp. 2.

Tang et al., "Linear Dimensionality Reduction Using Relevance Weighted LDA", Pattern Recognition, 2005, vol. 38, pp. 485-493, <http://staff.ustc.edu.cn/~ketang/papers/TangSuganYaoQin_PR04.pdf>.

Thomas et al., "Implementation of a Tight Glycaemic Control Protocol Using a Web-Based Insulin Dose Calculator", Anaesthesia, 2005, vol. 60, pp. 1093-1100.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Westbrook et al., "Errors in the Administration of Intravenous Medications in Hospital and the Role of Correct Procedures and Nurse Experience", BMJ Quality & Safety, 2011, vol. 20, pp. 1027-1034.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

* cited by examiner

ACOUSTIC FLOW SENSOR FOR CONTINUOUS MEDICATION FLOW MEASUREMENTS AND FEEDBACK CONTROL OF INFUSION

CROSS-REFERENCE TO RELATED APPLICATIONS

This application is a continuation of U.S. application Ser. No. 16/308,425, filed Dec. 7, 2018, entitled ACOUSTIC FLOW SENSOR FOR CONTINUOUS MEDICATION FLOW MEASUREMENTS AND FEEDBACK CONTROL OF INFUSION, which is a National Stage Entry of Application No. PCT/US2017/036619, filed Jun. 8, 2017, entitled ACOUSTIC FLOW SENSOR FOR CONTINUOUS MEDICATION FLOW MEASUREMENTS AND FEEDBACK CONTROL OF INFUSION, which claims benefit of U.S. Provisional Application No. 62/348,301, filed Jun. 10, 2016, entitled ACOUSTIC FLOW SENSOR FOR CONTINUOUS MEDICATION FLOW MEASUREMENTS AND FEEDBACK CONTROL OF INFUSION. The contents of the aforementioned application are hereby incorporated by reference in its entirety as if fully set forth herein. The benefit to the foregoing application is claimed under the appropriate legal bias, including, without limitation, under 35. U.S.C. § 119(e).

BACKGROUND OF THE INVENTION

Field of the Invention

The disclosure relates to flow detection systems and methods for operating an infusion pump which utilize a high-frequency acoustic, closed loop system to measure and control the volumetric flow rate of the infusion pump.

Background of the Invention

Infusion systems and methods often operate in an open loop configuration, without receiving feedback regarding the volume of fluid being delivered to the patient. These infusion systems and methods typically rely on tightly controlled tolerances to fabricate the individual components and assemblies of the infusion pumping system to maintain the accuracy of delivered medication over a prescribed time. The accuracy of the amount of the prescribed medication being delivered to the patient by current infusion systems and methods can vary over time due to the component degradation over the life of the infuser. Additionally, requirements for tight tolerances for the individual components of the pumping mechanism significantly increase the manufacturing and service cost of the infusion system. Other infusion systems and methods utilize varying ways of attempting to monitor the amount of the medication being delivered to the patient with one or more additional issues.

An infusion system and method is needed to reduce one or more issues associated with one or more of the current infusion systems and methods.

SUMMARY OF THE INVENTION

In one embodiment of the disclosure, an infusion system for automatically detecting and adjusting a volumetric flow rate delivered by an infusion pump is disclosed. The infusion system includes an infusion pump, a flow path, at least one upstream acoustic sensor, at least one downstream acoustic sensor, at least one processor, and at least one memory. The infusion pump is configured to pump infusion fluid. The infusion fluid is configured to be delivered by the infusion pump along the flow path. The upstream acoustic sensor is located at an upstream location of the flow path. The downstream acoustic sensor is located at a downstream location of the flow path. The downstream acoustic sensor is configured to detect an upstream acoustic signal emitted by the upstream acoustic sensor. The upstream acoustic sensor is configured to detect a downstream acoustic signal emitted by the downstream acoustic sensor. The processor is in electronic communication with the infusion pump, the upstream acoustic sensor, and the downstream acoustic sensor. The memory is in electronic communication with the processor. The memory includes programming code for execution by the processor. The programming code is configured to determine a volumetric flow rate of the infusion fluid along the flow path based on the upstream acoustic signal detected by the downstream acoustic sensor and on the downstream acoustic signal detected by the upstream acoustic sensor. The programming code is configured to determine the volumetric flow rate of the infusion fluid along the flow path based on a first phase delay of the upstream acoustic signal between the upstream acoustic sensor and the downstream acoustic sensor, and/or on a second phase delay of the downstream acoustic signal between the downstream acoustic sensor and the upstream acoustic sensor. The programming code is further configured to automatically adjust the infusion pump based on the determined volumetric flow rate, to achieve a desired volumetric flow rate of the infusion fluid along the flow path.

In another embodiment of the disclosure, a method for automatically detecting and adjusting a volumetric flow rate delivered by an infusion pump is disclosed. In one step, infusion fluid is delivered with an infusion pump along a flow path. In another step, an upstream acoustic signal emitted by at least one upstream acoustic sensor, located at an upstream location of the flow path, is detected with at least one downstream acoustic sensor located at a downstream location of the flow path. In an additional step, a downstream acoustic signal emitted by the downstream acoustic sensor, located at the downstream location of the flow path, is detected with the upstream acoustic sensor located at the upstream location of the flow path. In another step, a volumetric flow rate of the infusion fluid along the flow path is determined, with at least one processor, over each stroke of the infusion pump based on the upstream acoustic signal detected by the downstream acoustic sensor and on the downstream acoustic signal detected by the upstream acoustic sensor. The processor determines the volumetric flow rate of the infusion fluid along the flow path over each stroke of the infusion pump by determining a first phase delay of the upstream acoustic signal between the upstream acoustic sensor and the downstream acoustic sensor, or by determining a second phase delay of the downstream acoustic signal between the downstream acoustic sensor and the upstream acoustic sensor. In still another step, the infusion pump is automatically adjusted, with the processor, over each pumping cycle of the infusion pump based on the determined volumetric flow rate to achieve a desired volumetric flow rate of the infusion fluid along the flow path.

In still another embodiment of the disclosure, a non-transitory computer readable medium is disclosed. The non-transitory computer readable medium is configured to, using at least one processor, automatically detect and adjust a volumetric flow rate of infusion fluid delivered by an infusion pump. The non-transitory computer readable medium includes programming code to command the processor to determine, over each stroke of the infusion pump, the volumetric flow rate of the infusion fluid delivered by the infusion pump along a flow path. The programming code is configured to determine, over each stroke of the infusion pump, the volumetric flow rate based on an upstream acoustic signal emitted by at least one upstream acoustic sensor, located at an upstream location of the flow path, which is detected by at least one downstream acoustic sensor located at a downstream location of the flow path. The programming code is further configured to determine, over each stroke of the infusion pump, the volumetric flow rate based on a downstream acoustic signal emitted by the downstream acoustic sensor and detected by the upstream acoustic sensor. The programming code is configured to automatically adjust the infusion pump over each pumping cycle of the infusion pump, based on the determined volumetric flow rate, to achieve a desired volumetric flow rate of the infusion fluid along the flow path.

In certain embodiments, an infusion system can automatically control an infusion pump. The infusion system can include an infusion pump that can pump infusion fluid along a flow path. The infusion system can also include a first acoustic sensor positioned at a first location along the flow path, the first acoustic sensor can detect a first acoustic signal. The infusion system can further include a second acoustic sensor positioned at a second location downstream from the first acoustic sensor along the flow path. The second acoustic sensor can detect a second acoustic signal. The infusion system can also include a controller that can determine a first volumetric flow rate of the infusion fluid based on the detected first acoustic signal and the detected second acoustic signal. The controller can also control the infusion pump to pump infusion fluid at a second volumetric flow rate based on the detected first volumetric flow rate.

The infusion system of the preceding paragraph can have any sub-combination of the following features: wherein the first acoustic signal originated from the second acoustic sensor and the second acoustic signal originated from the first acoustic sensor; wherein the first acoustic sensor comprises a first transducer and the second acoustic sensor comprises a second transducer; wherein the first acoustic sensor comprises a first transmitter and a first receiver and the second acoustic sensor comprises a second transmitter and a second receiver; wherein the first receiver and the second receiver each comprise at least one noise cancelling component; wherein the first volumetric flow rate of the infusion fluid is calculated over each stroke of the infusion pump; wherein the first volumetric flow rate is determined based on a first phase delay associated the first acoustic signal; wherein the first volumetric flow rate is determined based on a second phase delay associated the second acoustic signal; wherein the first volumetric flow rate is determined based on a length between the first location and the second location; wherein the first volumetric flow rate is determined based on a first time it takes the first acoustic signal to travel between the second acoustic sensor and the first acoustic sensor; wherein the first volumetric flow rate is determined based on a first time it takes the second acoustic signal to travel between the first acoustic sensor and the second acoustic sensor.

In certain embodiments, a method of controlling an infusion pump can include detecting a first acoustic signal from a first acoustic sensor positioned at a first location along the flow path. The method can further include detecting a second acoustic signal from a second acoustic sensor positioned at a second location downstream from the first acoustic sensor along the flow path. The method can also include determining a first volumetric flow rate of the infusion fluid based on the detected first acoustic signal and the detected second acoustic signal. Moreover, the method can include changing the first volumetric flow rate to a second volumetric flow rate based on the determined first volumetric flow rate.

The method of the preceding paragraph can have any sub-combination of the following features: wherein the first acoustic signal originated from the second acoustic sensor and the second acoustic signal originated from the first acoustic sensor; wherein the first acoustic sensor comprises a first transducer and the second acoustic sensor comprises a second transducer; wherein the first acoustic sensor comprises a first transmitter and a first receiver and the second acoustic sensor comprises a second transmitter and a second receiver; wherein the first receiver and the second receiver each comprise at least one noise cancelling component; wherein the first volumetric flow rate of the infusion fluid is calculated over each stroke of the infusion pump; wherein the first volumetric flow rate is determined based on a first phase delay associated the first acoustic signal; wherein the first volumetric flow rate is determined based on a second phase delay associated the second acoustic signal; wherein the first volumetric flow rate is determined based on a length between the first location and the second location; wherein the first volumetric flow rate is determined based on a first time it takes the first acoustic signal to travel between the second acoustic sensor and the first acoustic sensor; wherein the first volumetric flow rate is determined based on a first time it takes the second acoustic signal to travel between the first acoustic sensor and the second acoustic sensor.

These and other features, aspects and advantages of the disclosure will become better understood with reference to the following drawings, description and claims.

DETAILED DESCRIPTION

The following detailed disclosure describes one or more modes of carrying out the invention. The disclosure is not to be taken in a limiting sense, but is made merely for the purpose of illustrating the general principles of the disclosure, since the scope of the disclosure is best defined by the appended claims. It is noted that the figures are purely for illustrative purposes and are not to scale. It is further noted that any portions of the embodiments of the below disclosure may be, in varying embodiments, combined in part or in full, one or more components may be added, or one or more components may be removed.

Figure 1:
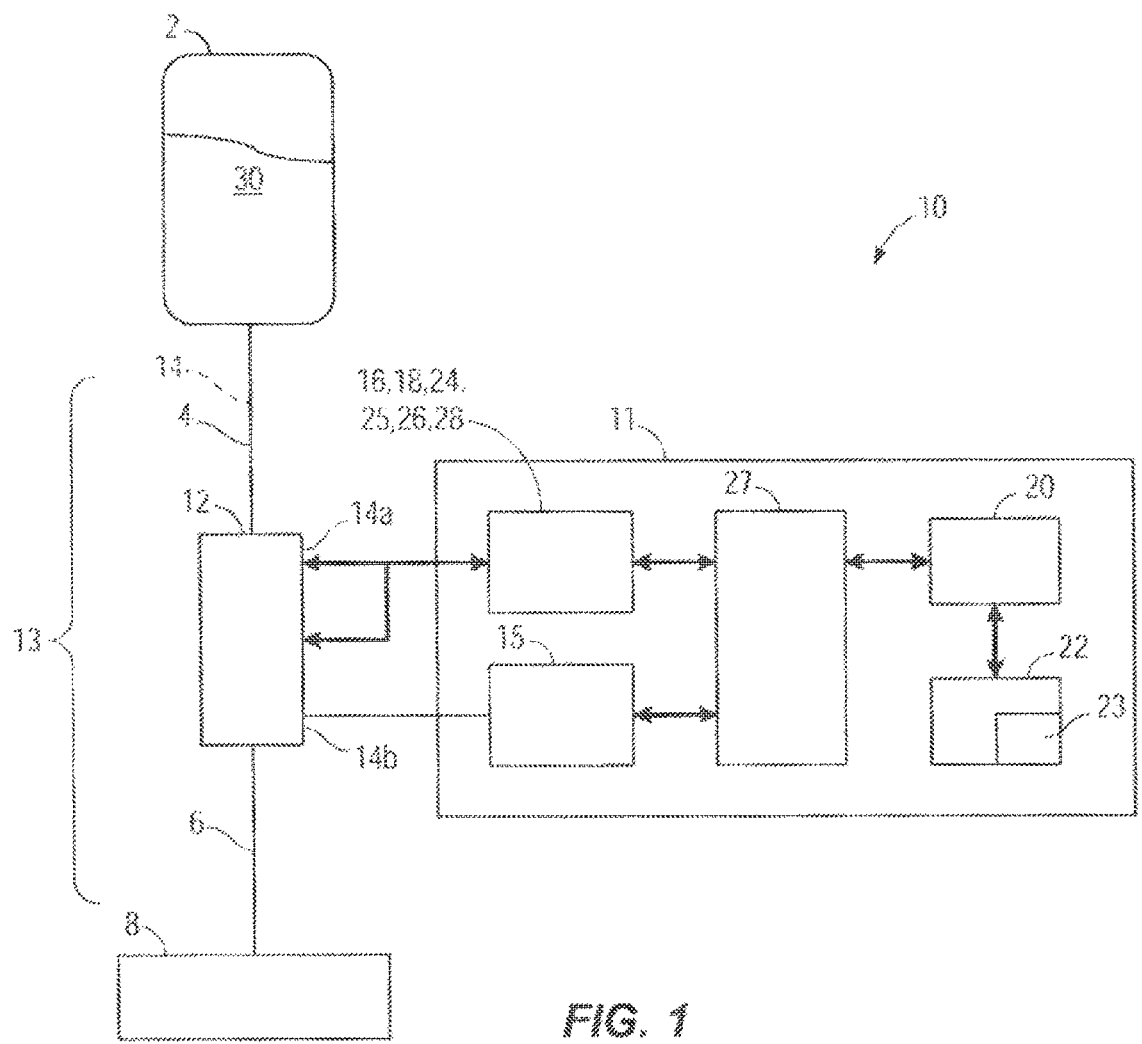
FIG. 1 illustrates one embodiment of a box diagram of an infusion system.

FIG. 1 illustrates an embodiment of a box diagram of an infusion system 10. The infusion system 10 can include an infusion pump or infuser 11 and an infusion set 13 that is inserted in, and is acted upon by the infusion pump 11. The infusion set 13 can include, among other elements, an inlet tube 4, an outlet tube 6 and a cassette 12. The infusion system 10 can also include an infusion pump 11 with an infusion pumping mechanism 15, a pump cassette 12, an infusion set 13 that has an internal flow path 14, at least one upstream acoustic sensor 16, at least one downstream acoustic sensor 18, at least one hardware processor 20, at least one memory (also referred to herein as a non-transitory computer readable medium) 22, programming code 23, a proximal air-in-line sensor 24, a proximal pressure sensor 25, a distal pressure sensor 26, and a distal air-in-line air sensor 28. Signals from the infusion pumping mechanism 15 and the sensors 16, 18, 24, 25, 26, 28 are acquired, conditioned if necessary, and sent to the hardware processor 20 by signal acquisition electronics 27 to monitor proper operation of fluid delivery. The hardware processor 20 can be programmed to execute programming code 23 or various algorithms stored in the memory 22 and can control operation of the pumping mechanism 15 through the driving electronics. The programming code or instructions can be implemented in C, C++, JAVA, or any other suitable programming languages. In some embodiments, some or all of the portions of the programmed instructions can be implemented in application specific circuitry 928 such as ASICs and FPGAs.

The infusion system 10 is configured to automatically detect and adjust a volumetric flow rate of infusion fluid 30 delivered by the infusion pump 11 along the flow path 14. In other embodiments, the infusion system 10 may include varying components varying in number, size, type, orientation, configuration, location, or function. For instance, in another embodiment the infusion system 10 may not utilize a pump cassette 12 (for example, see FIG. 2B and the description below).

Figure 1A:
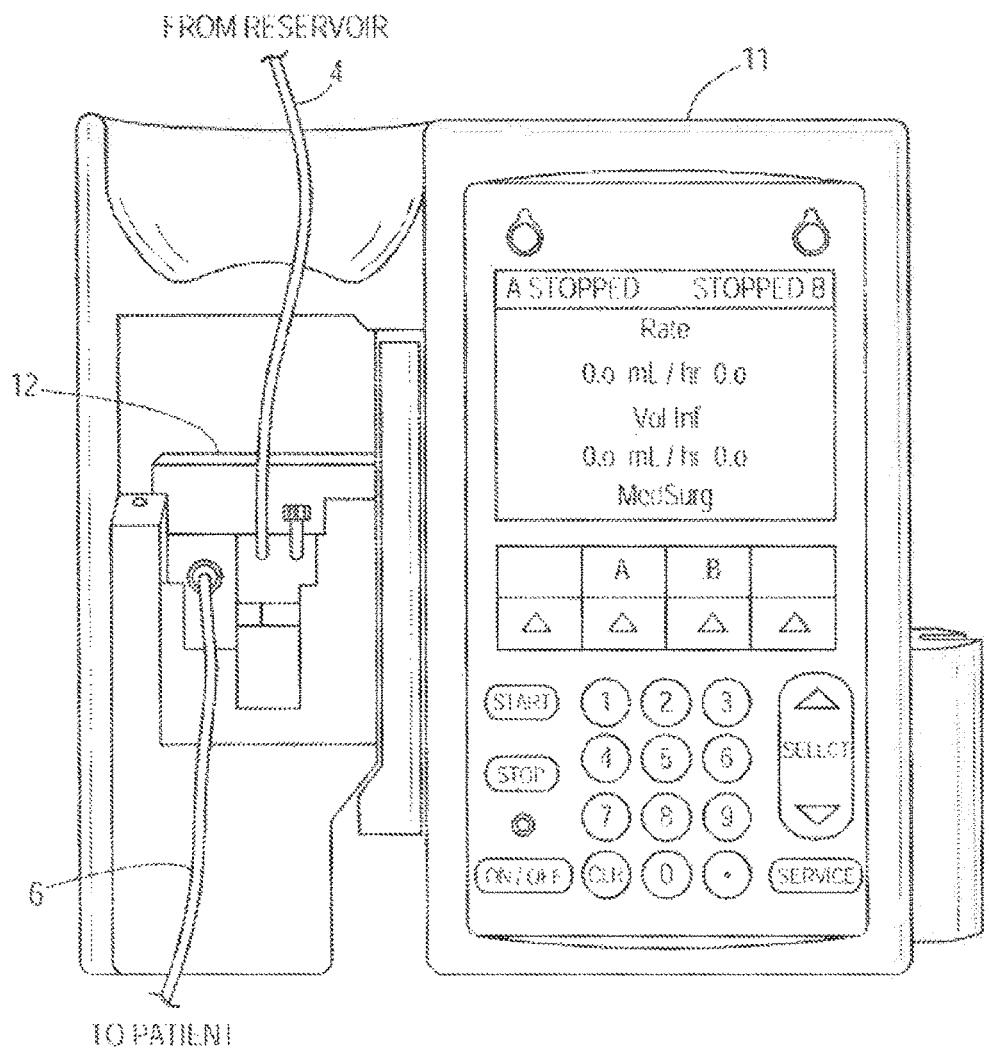
FIG. 1A illustrates one embodiment of a pictorial view of a front of an infusion pump with a pump cassette or infusion set cassette inserted into the infusion pump.

As shown collectively in FIGS. 1 and 1A, the infusion pump 11 is operatively coupled to the pump cassette 12. In other words, the cassette 12 is inserted in the infusion pump 11. The infusion pump 11 is configured to operate on the cassette 12 to pump the infusion fluid 30 from a source or reservoir 2, which can be a bag, vial or other container, through the inlet tube 4, at least one internal passageway of the cassette 12, and through the outlet tube 6 along the flow path 14, which may lead to a patient 8. In other embodiments, the flow path 14 may be a flow path outside the pump cassette 12 or the pump cassette 12 may not be present at all and the flow path 14 may be any flow path over which the infusion fluid 30 flows. The upstream acoustic sensor 16 is coupled with the pump cassette 12 and located at an upstream location 14a of the flow path 14 at or integrated with the proximal pressure sensor 25 which is coupled with the pump cassette 12. In other embodiments, the upstream acoustic sensor 16 may be located at or integrated with the proximal air-inline sensor 24 or located or integrated with varying components of the infusion system 10. The upstream acoustic sensor 16 may include one or more ultrasonic sensors or other types of acoustic sensor. Upstream and downstream are relative terms used herein to indicate the position of the sensors along the flow path. In an embodiment, the upstream sensor encounters the flow of fluid from the reservoir 2 before the downstream sensor.

In an embodiment, the downstream acoustic sensor 18 is coupled with the pump cassette 12 and located at a downstream location 14b of the flow path 14 at or integrated with the distal air-in-line sensor 28 which is coupled with the pump cassette 12. In other embodiments, the downstream acoustic sensor 18 may be located at or integrated with the distal pressure sensor 26 or located or integrated with varying components of the infusion system 10.

Figure 7:
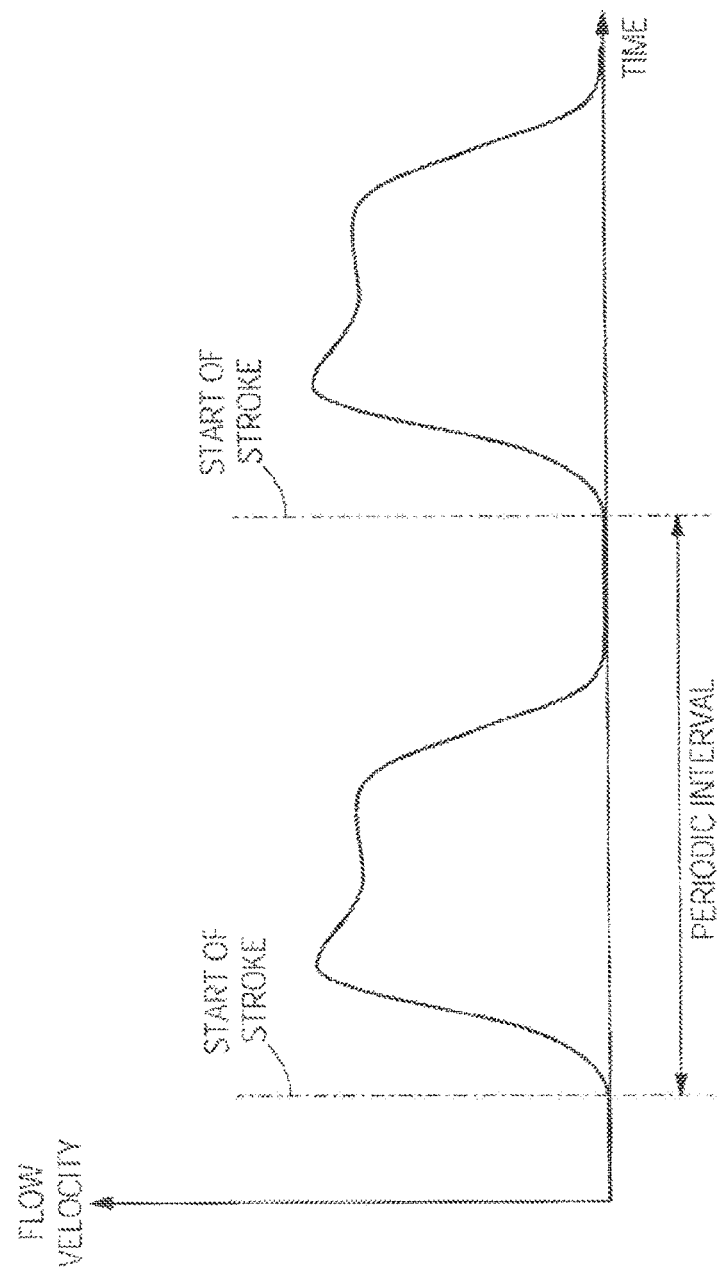
FIG. 7 illustrates one embodiment of a graph, with time plotted on the X-axis and flow velocity plotted on the Y-axis, showing a flow profile when pumping is done by intermittent movement of a pumping mechanism creating a periodic flow profile.

The downstream acoustic sensor 18 may include one or more ultrasonic sensors or other types of acoustic sensors. In an embodiment, the downstream acoustic sensor 18 is configured to detect an upstream acoustic signal emitted by the upstream acoustic sensor 16. The upstream acoustic sensor 16 can also be configured to detect a downstream acoustic signal emitted by the downstream acoustic sensor 18. In one embodiment, the upstream acoustic sensor 16 and the downstream acoustic sensor 18 may take turns, synchronized with the pumping mechanism of the infusion pump 11, transmitting their respective upstream acoustic signal and downstream acoustic signal. The hardware processor 20 can calculate the flow rate of the infusion fluid by integrating the phase delay measurement between the upstream and downstream signals over each periodic pumping interval. The pumping mechanism 15 operates in a periodic manner, the flow measurement is obtained by the sensors 16 and 18, and the flow is calculated by integration of the phase delay measurement over each individual periodic pumping interval as seen in FIG. 7. The flow measurement obtained by the sensors 16 and 18 can be synchronized with the period interval of the pumping mechanism 15 by the hardware processor 20 which determines the phase delay between the upstream and downstream signals over each stroke of the pumping mechanism 15 (shown in FIG. 1) and uses the phase delay to determine the volumetric flow rate of the infusion fluid over each stroke of the pumping mechanism 15. Moreover, the hardware processor 20 (shown in FIG. 1) is configured to make flow rate adjustments to the infusion fluid over each pumping cycle based on the determined flow rate over each stroke of the pumping mechanism 15. Furthermore, the hardware processor 20 (shown in FIG. 1) may average the determined flow rates over a multitude of pump cycles and adjust the flow rate of the infusion fluid accordingly. In such manner, rapid update rate fluid delivery pumping correction can be achieved utilizing periodic sampling over the pumping period.

It is noted that the movement of infusion fluid into an IV line is modulated by numerous items. The items that modulate the fluid flow are complex including but not limited to plunger movement, pump valve operation, bag height, and patient relation to the pump chamber. Many of the dynamic changes are periodic in nature as depicted in FIG. 7. This periodicity can be utilized to create a more rapid update rate for average flow. To have a reading of average flow by conventional means it may require averaging the readings over several periodic periods. However, by gating the averaging by the periodic period the average can be known in one periodic period. This can allow the control of fluid delivery to be corrected much more quickly. In some embodiments, this is much more accurate for determining the flow rate than conventional methods. In such manner, the hardware processor of the infusion system can calculate the phase delay over each stroke to determine the flow rate over each stroke and by subsequently adjusting the flow rate over each pumping cycle based on the determined flow rate, the infusion system has superior flow rate accuracy over conventional systems and methods. This allows for the use of the infusion system over a much longer period of time as diaphragm deterioration and other deterioration of the components of the infusion system may be accounted for in real-time during each pumping cycle of the pumping mechanism by adjusting the flow rate of the infusion fluid accordingly.

In another embodiment, the upstream acoustic sensor 16 and the downstream acoustic sensor 18 may continuously transmit their respective upstream acoustic signal and downstream acoustic signal or the measurements may occur over a given number of periodic intervals. One skilled in the art will recognize that the terms "upstream" and "downstream", as used herein, are terms that describe the location of one component of the system with respect to one or more other components of the system. The flow path 14 can be thought of as a river where fluid is normally flowing from the source 2 to the patient 8. In an embodiment, the upstream acoustic sensor 16 is located between the pumping mechanism 15 and the reservoir 2 or upstream of the pumping mechanism 15, and the downstream acoustic sensor 18 is located between the pumping mechanism 15 and the patient 8 or downstream of the pumping mechanism 15. The upstream acoustic sensor 16 is located upstream along the normal flow path 14 from the downstream acoustic sensor 18. One skilled in the art will also appreciate that the upstream and downstream acoustic sensors 16 and 18 could be referred to as proximal and distal acoustic sensors respectively.

Figure 2:
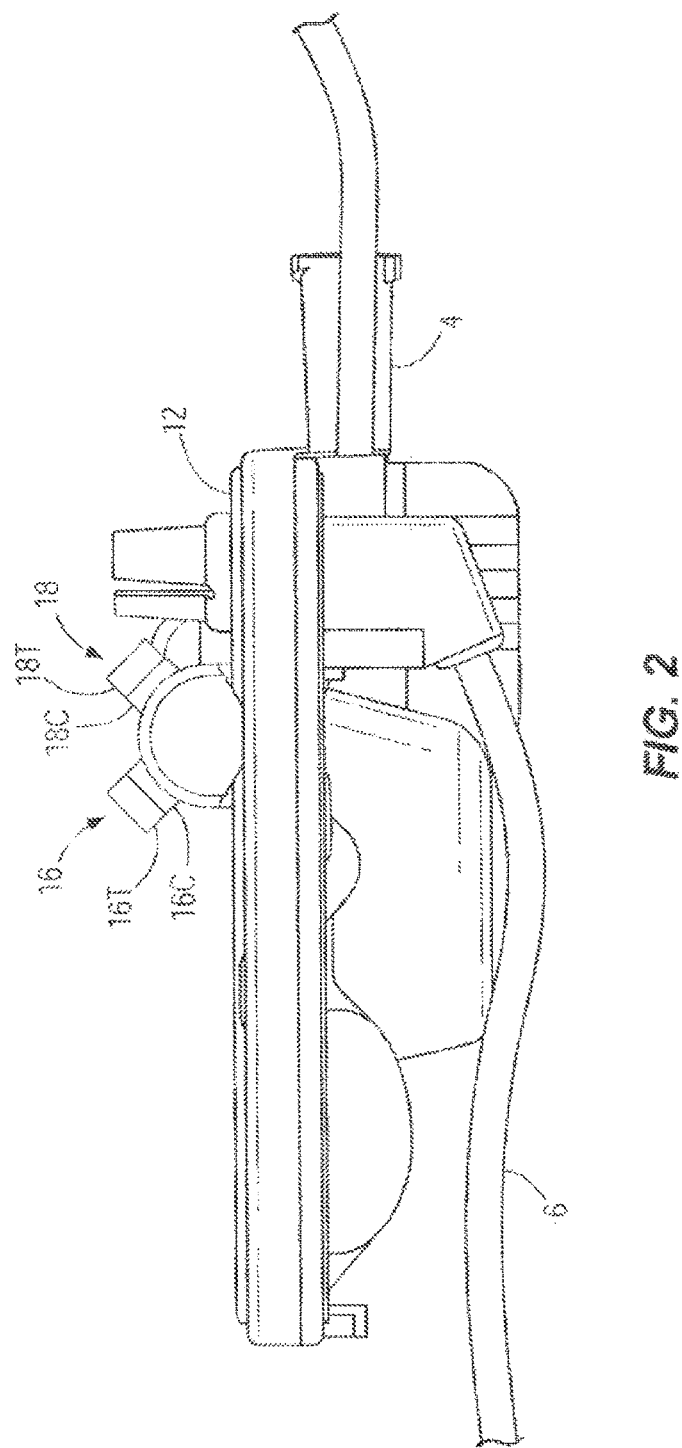
FIG. 2 illustrates one embodiment of a side-view of an infusion set cassette illustrating configuration and placement of ultrasonic acoustic transducers.
Figure 2A:
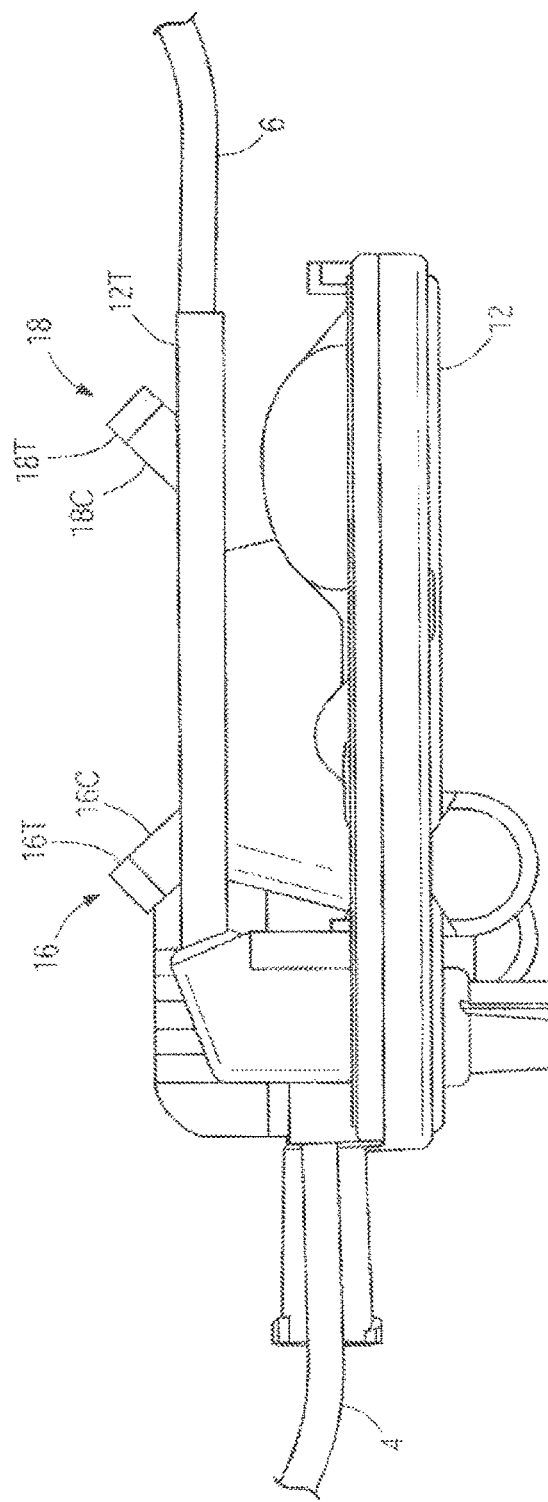
FIG. 2A illustrates another embodiment of a side view of an infusion set cassette showing configuration and placement of ultrasonic acoustic transducers.

FIGS. 2 and 2A illustrate two different possible configurations and placements of acoustic sensors 16 and 18 against or adjacent to a cassette 12 as shown relative to the inlet tube 4 and the outlet tube 6. The acoustic sensors 16 and 18 are non-invasive ultrasonic transducers 16T and 18T. The transducers 16T and 18T have double function of emitters and receivers. The transducers 16T and 18T contact the cassette 12 by means of coupling elements. The coupling elements 16C and 18C are made of a compliant material and ensure good acoustic contact. In one embodiment, the transducers 16T and 18T with their coupling elements 16C and 18C are part of the pump 11 (shown in FIG. 1).

Figure 2B:
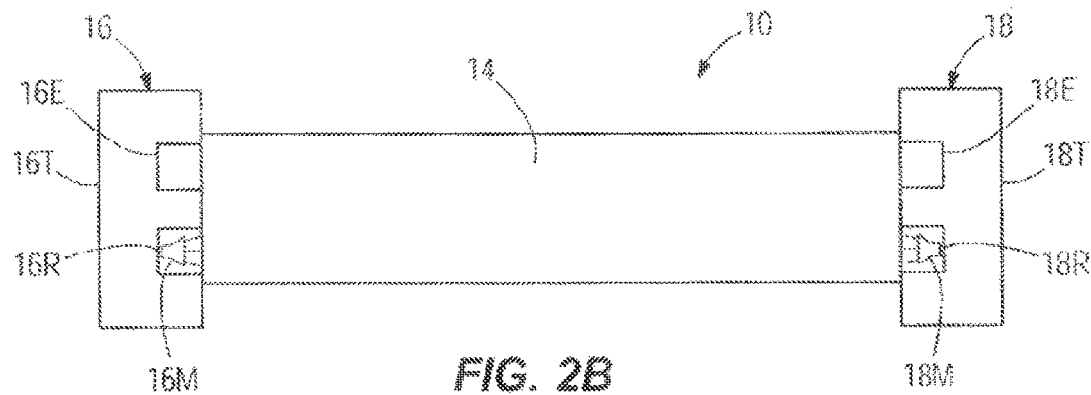
FIGS. 2B-2D illustrate various embodiments of a partial cross-sectional view of a flow path of an infusion system showing the configuration and placement of ultrasonic acoustic transducers.

FIG. 2B illustrates one embodiment of a cross-section view through a portion of an infusion system 10 in which the disclosure could be implemented showing the flow path 14, the one upstream acoustic sensor 16, and the one downstream acoustic sensor 18. The upstream acoustic sensor 16 includes a first transducer 16T that includes a transmitter 16E and a first receiver 16R which are shown in greater detail with their accompanying electronics in FIG. 3. The first receiver 16R includes a noise cancelling component such as a noise cancelling microphone 16M. Similarly, the downstream acoustic sensor 18 includes a second transducer 18T that includes a transmitter 18E and a second receiver 18R which are shown in greater detail with their accompanying electronics in FIG. 3. The second receiver 18R can also include a noise cancelling component such as a noise cancelling microphone 18M. In additional embodiments, the upstream acoustic sensor 16 and the downstream acoustic sensor 18 may further vary.

Figure 2C:
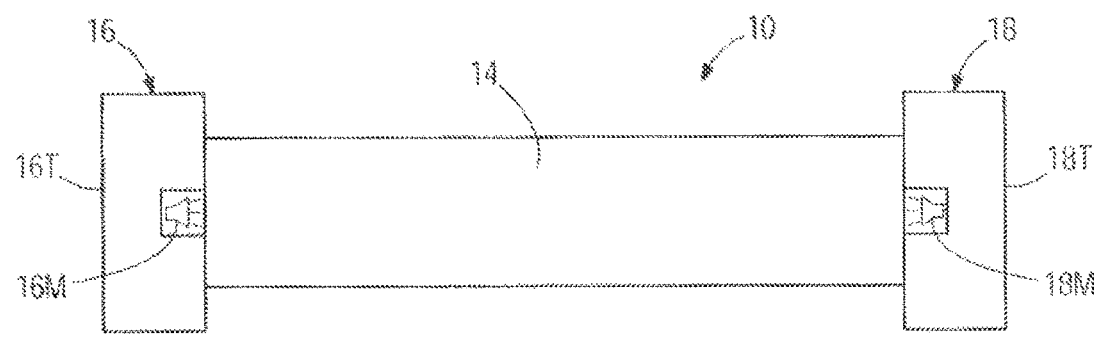

FIG. 2C illustrates another embodiment of a cross-section view through a portion of an infusion system 10 in which the disclosure could be implemented showing the flow path 14, the upstream acoustic sensor 16, and the downstream acoustic sensor 18. The upstream acoustic sensor 16 can include a first transducer 16T, and the downstream acoustic sensor 18 includes a second transducer 18T. The first transducer 16T and the second transducer 18T may each include or be connected to a noise cancelling component such as noise cancelling microphones 16M and 18M. In additional embodiments, the upstream acoustic sensor 16 and the downstream acoustic sensor 18 may further vary.

In another embodiment shown in FIG. 2A, the existing cassette 12 is enhanced by the addition of a straight rigid tube 12T with a precise internal bore. The tube 12T can be part of the cassette 12 as an extension of its outlet port. The transducers 16T and 18T make contact with the tube 12T or are coupled to the tube 12T by the coupling elements 16C and 18C.

Figure 2D:
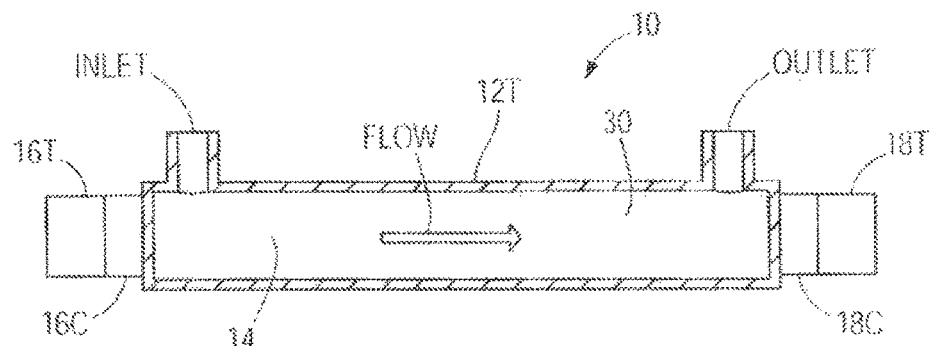

In another embodiment shown in FIG. 2D, the infusion system 10 may or may not include a cassette, but includes in the flow path 14 a straight rigid tube 12T that has a precisely dimensioned internal bore. If the system 10 includes a cassette (shown in FIG. 1 as cassette 12), the rigid tube 12T is located downstream of the cassette and is connected to or integrated with an outlet tube (shown in FIG. 1 as outlet tube 6). If the system does not include a cassette, the tube 12T can be located downstream of whatever pumping mechanism (shown in FIG. 1 as pumping mechanism 15) exists. In the case of gravity flow where no pumping mechanism exists other than gravity, the tube 12T can be located between the source (shown in FIG. 1 as source 2) and the patient (shown in FIG. 1 as patient 8), downstream of a conventional clamp or valve (not shown) for controlling the flow of the infusion fluid 30. The infusion fluid 30 enters the tube 12T through an inlet and flows to an outlet. The upstream transducer 16T is coupled to the tube 12T adjacent to the inlet by a coupling element 16C. The downstream transducer 18T is coupled to the tube 12T adjacent to the outlet by a coupling element 18C.

Figure 3:
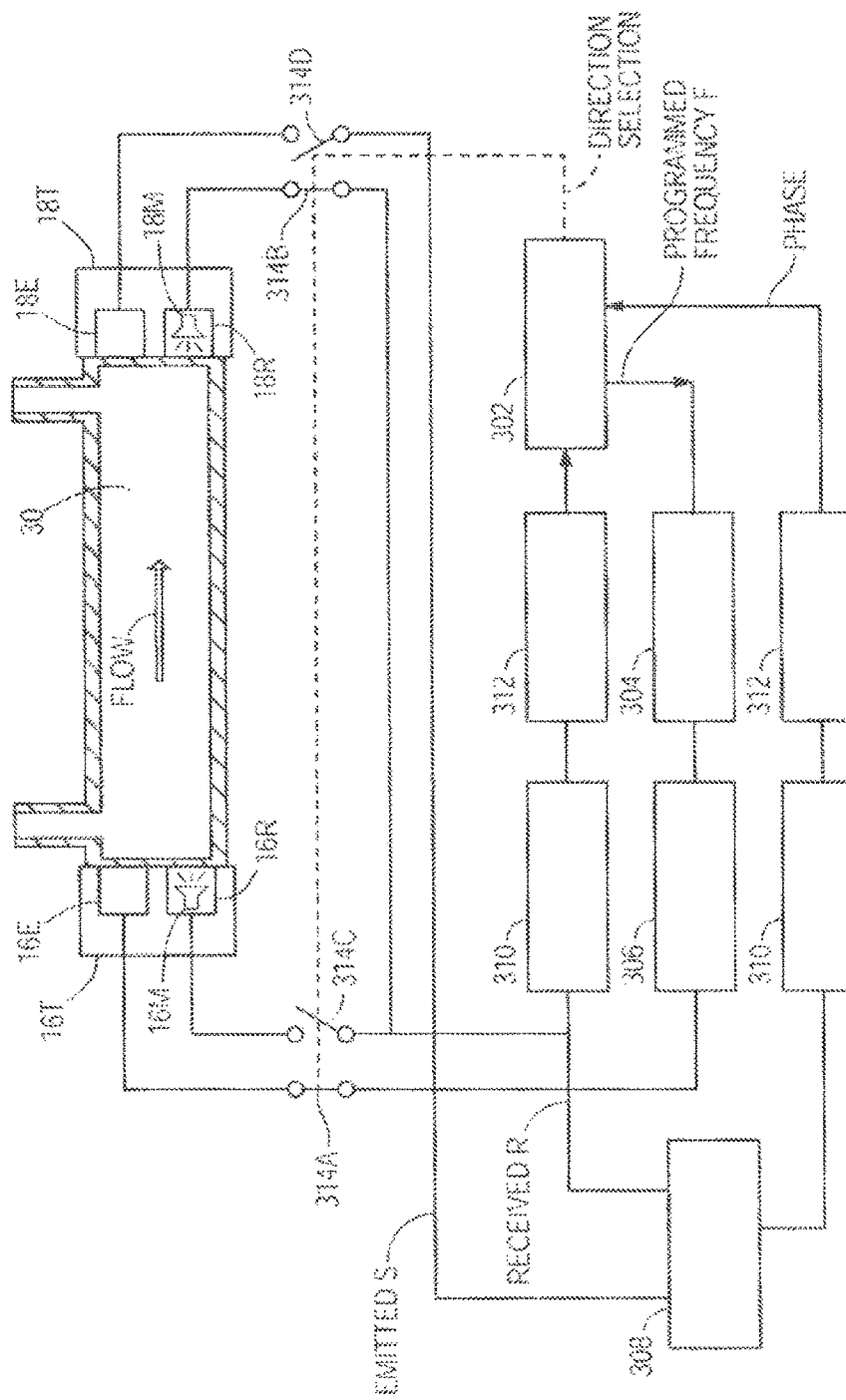
FIG. 3 illustrates one embodiment of a simplified circuit diagram showing an acoustic flow sensing system.

Taking as an example the embodiment in FIG. 2D, FIG. 3 shows one embodiment of the flow sensor circuits which may be utilized to monitor the flow rate of the infusion fluid 30. In this case, the transducers 16T, 18T can be transducers or can each include separate emitters or transmitters 16E, 18E and receivers 16R, 18R. The transmitter and receiver function can be accomplished by the same transducer or by separate transducers performing each a single function. The transmitters 16E and 18E can emit ultrasonic signals and the receivers 16R and 18R receive the ultrasonic signals from the transmitters 18E and 16E. The receivers 16R and 18R can include noise cancelling components such as noise cancelling microphones 16M and 18M. The microcontroller 302 (also referred to as a hardware processor herein which could include one or more hardware processors) commands a frequency generator 304 to generate a voltage signal with the programmed frequency f. A driver 306 amplifies the signal and sends it to the emitter 16E of one of the transducers 16T. The emitter 16E generates an ultrasonic signal S that propagates through the fluid 30 and is detected by the receiver 18R at the other end of the tube, which generates a voltage signal proportional to the received ultrasonic signal R. The emitted signal S and the received signal R are fed to a phase comparator 308 that generates a signal proportional to the phase difference between the two signals. A signal conditioning stage 310 amplifies and filters the signal and sends it to an analog to digital converter 312 that converts it to a digital phase signal received by the microcontroller 302. The microcontroller 302 controls the switches 314A, 314B, 314C, 314D that select the propagation direction of the ultrasonic signal. In this embodiment the signal S is emitted alternatively with and against the flow direction. When the signal S is to be emitted with the direction of fluid flow, the normally closed switches 314A and 314B are closed and the normally open switches 314C and 314D are open; and when the signal S is to be emitted in the opposite direction, against the direction of fluid flow, the microcontroller 302 opens switches 314A and 314B and closes switches 314C and 314D. The transmitter and receiver transducers can be piezoelectric, electromagnetic, or microelectromechanical systems (MEMS) based in construction.

Figure 3A:
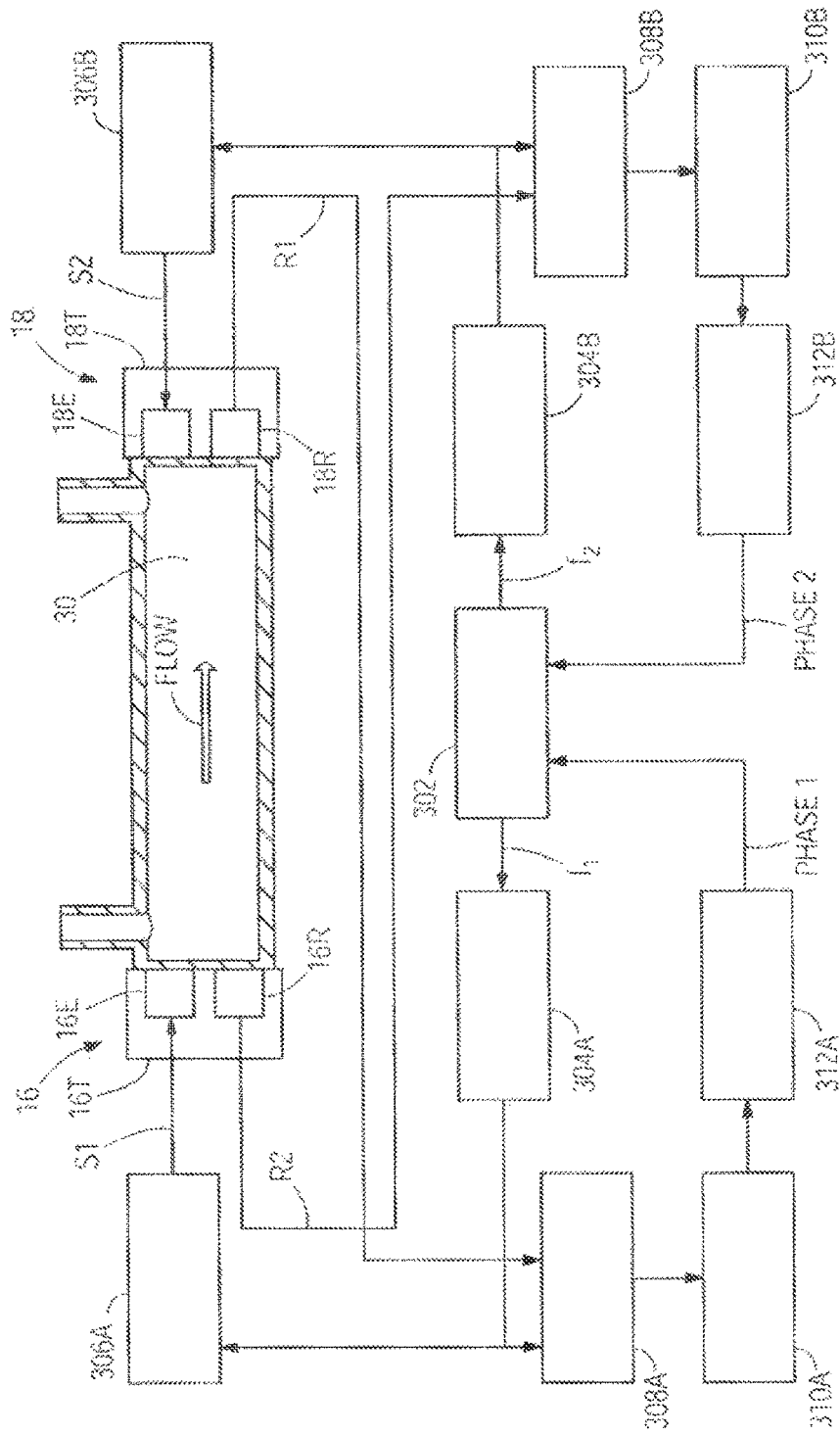
FIG. 3A illustrates another embodiment of a simplified circuit diagram showing an acoustic flow sensing system.

Taking as an example the embodiment of FIG. 2D, FIG. 3A shows another embodiment of the flow sensor circuits which may be utilized to monitor the flow rate of the infusion fluid 30. In this case the transducers 16T and 18T still contain separate emitters 16E and 18E and receivers 16R and 18R, but the transducers 16T and 18T are operated continuously. In other words, the case of simultaneous transmission with separate transmitter and receiver transducers is illustrated. There are two separate channels, one for the acoustic signal propagating against the flow and one for the acoustic signal propagating with the flow. The programmed frequencies $f_1$ and $f_2$ of the signals S1 and S2 in the two channels are different, so they can be separated by the phase comparators 308A and 308B. The microcontroller 302 commands a frequency generator 304A to generate a voltage signal with the programmed frequency $f_1$. A driver 306A amplifies the signal S1 and sends it to the emitter 16E of one of the transducers 16T. The emitter 16E generates an ultrasonic signal that propagates through the fluid 30 and is detected by the receiver 18R at the other end of the tube, which generates a voltage signal proportional to the received ultrasonic signal R1. The emitted signal S1 and the received signal R1 are fed to a phase comparator 308A that generates a signal proportional to the phase difference between the two signals. A signal conditioning stage 31 OA amplifies and filters the signal and sends it to an analog to digital converter 312A that converts it to a digital phase signal received by the microcontroller 302. The microcontroller 302 further commands a frequency generator 304B to generate a voltage signal with the programmed frequency $f_2$. A driver 306B amplifies the signal S2 and sends it to the emitter 18E of one of the transducers 18T. The emitter 18E generates an ultrasonic signal that propagates through the fluid 30 and is detected by the receiver 16R at the other end of the tube, which generates a voltage signal proportional to the received ultrasonic signal R2. The emitted signal S2 and the received signal R2 are fed to a phase comparator 308B that generates a signal proportional to the phase difference between the two signals. A signal conditioning stage 31 OB amplifies and filters the signal and sends it to an analog to digital converter 312B that converts it to a digital phase signal received by the microcontroller 302. The transmitter and receiver transducers can be piezoelectric, electromagnetic, or microelectromechanical systems (MEMS) based in construction.

Figure 3B:
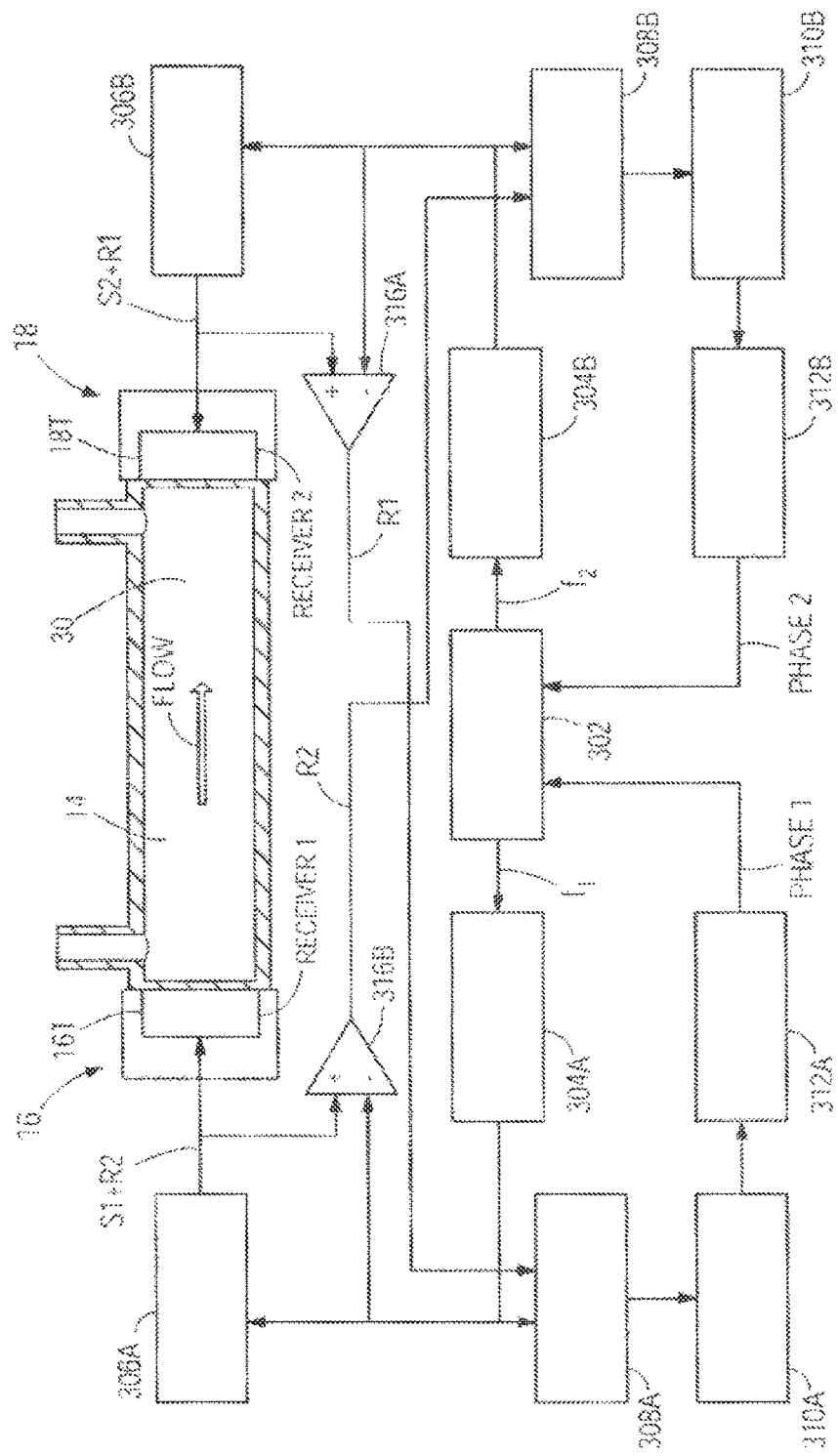
FIG. 3B illustrates still another embodiment of a simplified circuit diagram showing an acoustic flow sensing system.

Again taking as an example the embodiment of FIG. 2B, FIG. 3B shows another embodiment of the flow sensor circuits which may be utilized to monitor the flow rate of the infusion fluid 30. In this case, the transducers 16T and 18T perform both functions of emitting and receiving the ultrasonic signals. The transducers 16T and 18T transmit simultaneously and are operated continuously. There are still two separate channels. The frequencies f1, f2 of the signals S1 and S2 in the two channels are different, so they can be separated by the phase comparators 308A and 308B. The voltage at the terminals of each of the transducers 16T and 18T is the sum of the emitted signals S1 and S2 voltages from the drivers 306A and 306B and the voltages generated by the transducers 16T and 18T, which is proportional to the received signals R2 and R1. Difference amplifiers 316A and 316B subtract the emitted signals S1 or S2 from this sum, outputting the received signals R2 or R1 respectively. The microcontroller 302 (also referred to as a processor herein which could include one or more processors) commands frequency generator 304A to generate a voltage signal with the programmed frequency $f_1$. A driver 306A amplifies the signal S1 and sends it to the transducer 16T. The transducer 16T generates an ultrasonic signal that propagates through the fluid 30 and is detected by the transducer 18T at the other end of the tube, which generates a voltage signal of the sum of the received ultrasonic signal R1 and the signal S2 transmitted by the transducer 18T. Difference amplifier 316A subtracts the emitted signal S2 from this sum, outputting the received signal R1. The emitted signal S1 and the received signal R1 are fed to a phase comparator 308A that generates a signal proportional to the phase difference between the two signals. A signal conditioning stage 310A amplifies and filters the signal and sends it to an analog to digital converter 312A that converts it to a digital phase signal received by the microcontroller 302. The microcontroller 302 further commands frequency generator 304B to generate a voltage signal with the programmed frequency $f_2$. A driver 306B amplifies the signal S2 and sends it to the transducer 18T. The transducer 18T generates an ultrasonic signal that propagates through the fluid 30 and is detected by the transducer 16T at the other end of the tube, which generates a voltage signal of the sum of the received ultrasonic signal R2 and the signal S1 transmitted by the transducer 16T. Difference amplifier 316B subtracts the emitted signal S1 from this sum, outputting the received signal R2. The emitted signal S2 and the received signal R2 are fed to a phase comparator 308B that generates a signal proportional to the phase difference between the two signals. A signal conditioning stage 310B amplifies and filters the signal and sends it to an analog to digital converter 312B that converts it to a digital phase signal received by the microcontroller 302. The transmitter and receiver transducers can be piezoelectric, electromagnetic, or microelectromechanical systems (MEMS) based in construction.

As shown in FIG. 1 (and as further detailed in other embodiments herein using the same or different reference numbers), the hardware processor 20 is in electronic communication with the infusion pump 11, the upstream acoustic sensor 16, the downstream acoustic sensor 18, the one memory 22, the proximal air-in-line sensor 24, the proximal pressure sensor 25, the distal pressure sensor 26, and the distal air-in-line air sensor 28. The memory 22 contains the programming code 23 which is configured to be executed by the processor 20. The programming code 23 is configured to determine the volumetric flow rate of the infusion fluid 30 along the flow path 14 based on the upstream acoustic signal detected by the downstream acoustic sensor 18 and on the downstream acoustic signal detected by the upstream acoustic sensor 16, and to automatically adjust the infusion pump 11, based on the determined volumetric flow rate, to achieve a desired volumetric flow rate of the infusion fluid 30 along the flow path 14.

In the embodiments of FIGS. 3, 3A and 3B, the hardware processor 20 executing the programming code 23 (shown in FIG. 1) can determine the volumetric flow rate of the infusion fluid 30 along the flow path 14 based on a first phase delay of the upstream acoustic signal between the one upstream acoustic sensor 16 and the downstream acoustic sensor 18, or on a second phase delay of the downstream acoustic signal between the downstream acoustic sensor 18 and the upstream acoustic sensor 16.

In the embodiment of FIG. 1, the hardware processor 20 executing the programming code 23 is configured to determine the volumetric flow rate of the infusion fluid 30 along the flow path 14 by using the algorithm Q=V*A. In the algorithm, Q includes the volumetric flow rate, V includes a velocity of the infusion fluid 30 generated by the infusion pump 11, and A includes a cross-sectional area of the flow path 14. Moreover, $V=(L/2)*(1/t_1-1/t_2)$, wherein L includes a length between the upstream location 14a and the downstream location 14b, $t_1$ includes a first time it takes the upstream acoustic signal to travel from the one upstream acoustic sensor 16 to the downstream acoustic sensor 18, and $t_2$ includes a second time it takes the downstream acoustic signal to travel from the downstream acoustic sensor 18 to the one upstream acoustic sensor 16. In other words, $t_1-t_2$ can be thought of as the transit time of the signal or delta t. The distance between the sensors divided by delta t is the speed of the flow stream. The speed times the area of flow path equals the volumetric flow rate.

Figure 4:
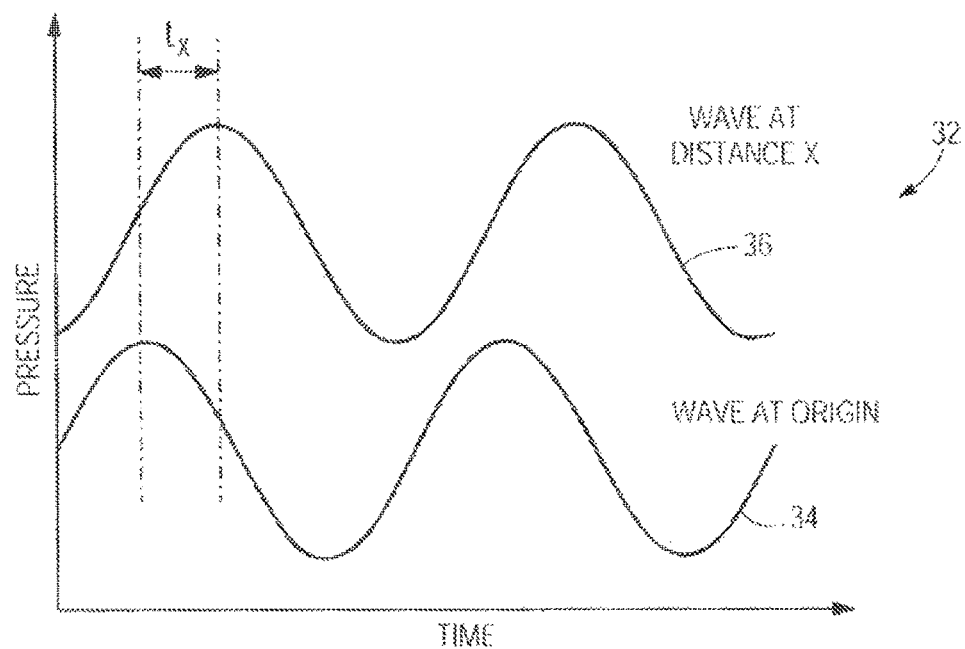
FIG. 4 illustrates one embodiment of a graph showing two acoustic pressure function curves, with time plotted on the X-axis and pressure plotted on the Y-axis, and a phase delay (difference between the received signal and the emitted signal) between the pressure function curves.

FIG. 4 illustrates a graph 32 of one embodiment of two acoustic pressure function curves 34 and 36 plotting time on the X-axis and pressure on the Y-axis to show the phase delay between the pressure function curves 34 and 36. Acoustic pressure function curve 34 includes the pressure wave at the origin of the upstream acoustic sensor 16 or 16T of FIG. 28. Acoustic pressure function curve 36 includes the pressure wave at distance x from the origin of the downstream acoustic sensor 18 or 18T of FIG. 2B. There is a delay time $t_x$ between the two acoustic pressure function curves 34 and 36. The two acoustic pressure function curves 34 and 36 represent periodic variations in time and space of the pressure in the liquid. It can be assumed that the pressure at the source is a simple sinusoidal function represented by $P(0,t)=P_0 \sin(2*\pi f*t)$, where $P_0$ includes pressure amplitude, f includes frequency of the sound wave, and t includes time.

At the distance x, the wave 36 is delayed by the time $t_x$ or, to express it in another way, the argument of the sine function is changed by the phase angle φ so that $P(x,t)=P_0 \sin[2*\pi*f*(t-t_x)]=P_0 \sin(2*\pi*t+\varphi)$. Using an electronic circuit called a phase discriminator, which is known in the art, to measure the phase angle between the two waves, the delay time between the wave 34 emitted and the wave 36 received at a certain distance may be calculated as being $t_x=\varphi/2*\pi*f$. In order to reduce the size of the measurement apparatus, shorter time measurements may be required due to the short distance between the transmitter and receiver. These shorter time measurements over the shorter distances can be accomplished through the use of the phase discriminator. In order to increase the resolution of the fluid flow without restricting the area of the flow channel a differential measurement is used. This measurement is done by determining the phase delay between the transmitter and receiver of a continuous signal. To convert this phase angle measurement to fluid speed it is necessary to take the period of the repetitive signal times the angle, according to the $t_x$ equation shown above.

For example, in the case of a short distance between the transmitter and receiver (less than a full cycle), given a predetermined/designed oscillator frequency f=5 MHz and a measured phase delay angle of 12 degrees, the method might determine:

Calculated time delay $t_x=-\varphi/2*\pi*f$ $tx=-12$ deg./$(2\pi 5$ MHz$)=42$ nsecs Thus, this method allows a small time delay to be measured. Utilization of signal phase shift allows measurement of a very small time delay. Advantageously, this can translate into accurate measurements over very short distances too. This is accomplished by utilizing a carrier signal phase shift between the signal emitted by the transmitter source to the signal at the receiver. The process described herein can be further illustrated in FIGS. 4 and 5.

The determined time delay can be used to determine the velocity V of the fluid, which in turn can be used to determine the volumetric flow rate Q. An illustration of velocity computation follows with a hypothetical numerical example where: $V=(L)*(1/t_1-1/t_2)$; $tx=(1/t_1-1/t_2)$; and L=distance between transmitter and receiver.

In a phase approach, over longer distances than the example above, several full cycles may exist between the transmitter and the receiver due to the distance or length L between them. For purposes of illustration below we will utilize 50 full cycles, plus a partial cycle that is measured as a phase delay. Assuming L is predetermined or designed to equal 0.005 m, the frequency of the carrier is 10 kHz, and φ=143 deg (measured):

Given the above $t_x$ will be:
(converting the angle to time)

$tx=(143$ deg$+50*360$ deg$)/2*\pi*10$ kHz$=835\mu S$ (then converting the time to velocity)

$$V = \frac{.005 \text{ m}}{tx} = 5.98 \text{ m/s}$$

Area, A, is the cross sectional area of the flow path (in this example the flow path is a tube or tubing with an inside diameter of 0.0003 meters)

$$\text{Area} = \left(\frac{.0003 \text{ m}}{2}\right)^2 * \pi = 0.071 \text{ mm}^2$$

This gives the volumetric flow rate Q=V*A $Q=V*$Area$=1523$ ml/hr

In the above equation, Q includes the volumetric flow rate, V includes a velocity of the infusion fluid 30 generated by the infusion pump 11, and A includes a cross-sectional area of the flow path 14.

So to review and summarize, the overall time propagation of the sound waves 34 and 36 will be affected by the flow of the fluid through the tubing and/or channel. There will be a difference in the delays since the propagation occurs faster downstream than upstream so that $t_1=L/C+V$, and $t_2=L/C-V$, wherein $t_1$ includes the time of sound propagation downstream, $t_2$ includes the time of sound propagation upstream, L includes a length of sound propagation path in the fluid channel, C includes sound velocity in the fluid, and v includes a velocity of fluid generated by the infuser. If the times are known, the following equation can be used $1/t_1 - 1/t_2 = (2*V)/L$. From this equation, the following equation can be obtained $V=(L/2)*(1/t_1-1/t_2)$. If the cross section area of the flow path A is known, the volumetric flow rate Q can be calculated using the equation $Q=V*A$. In the embodiment of FIG. 1, the hardware processor 20 executing the programming code 23 can determine the volumetric flow rate of the infusion fluid 30 along the flow path 14 based on the phase delay by using the equations above.

Figure 5:
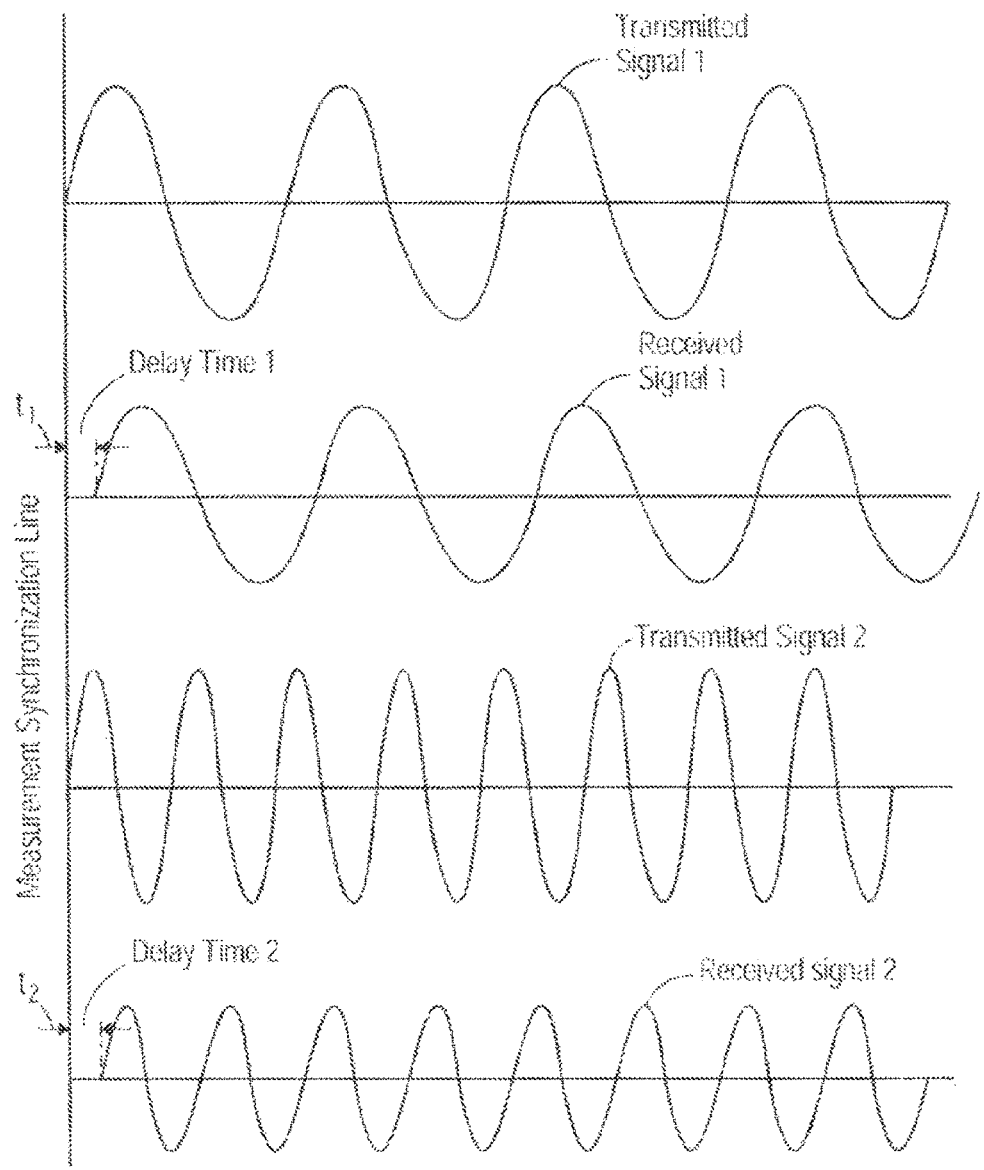
FIG. 5 illustrates one embodiment of a set of graphs in which two different frequencies are transmitted, received, and processed by two different transducers respectively.

FIG. 5 illustrates one embodiment of a set of graphs in which two different frequencies are transmitted, received, and processed by two different transducers respectively. The graphs depict the varying phase delays of the differing frequencies.

Figure 6:
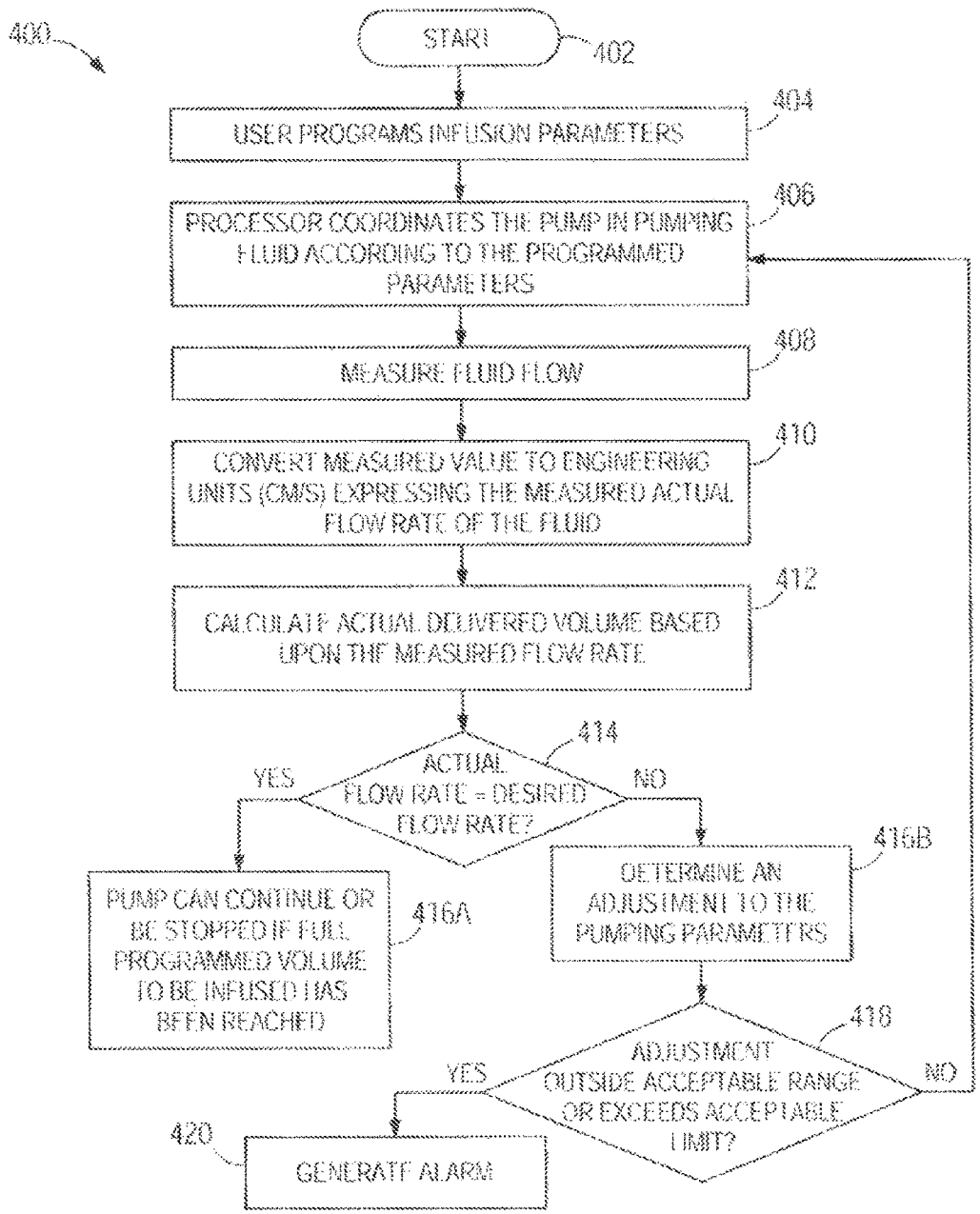
FIG. 6 illustrates one embodiment of a flowchart showing a method of automatically detecting and adjusting a volumetric flow rate delivered by an infusion pump.

FIG. 6 illustrates a flowchart of one embodiment of a method 400 of automatically detecting and adjusting a volumetric flow rate delivered by an infusion pump. FIG. 6 can also be thought of as a block diagram of closed loop control using flow sensing transduces. The method 400 may utilize any of the infusion systems disclosed herein. In other embodiments, the method 400 may utilize varying infusion systems. The method can start at node 402. In step 404, the infusion parameters including desired fluid flow rate, duration and dose are programmed by the user. Initially prompted by a start command from a user, in step 406, the hardware processor coordinates the pump in pumping fluid according to the programmed parameters. In step 408, the fluid flow is measured as described above and further explained with reference to FIG. 6A below. In step 410, the measured value is converted to engineering units (cm/s, m/s, etc.) expressing the measured actual flow rate of the fluid. Scaling based on the physical dimensions of the tube or flow channel and time offsets may be utilized. In step 412, the actual delivered volume is calculated based upon the measured flow rate and in step 414, the actual delivered volume is compared to the programmed or desired volume based upon the programmed delivery flow rate. If the actual flow rate is equal to the desired flow rate and thus the delivered volume is correct, then the method proceeds to step 416A and the pump can continue as is or be stopped if the full programmed volume to be infused has been reached. If the actual flow deviates or is not equal to the desired flow and thus the delivered volume is incorrect, the method proceeds to step 416B where an adjustment to the pumping parameters such as the programmed or desire flow rate is determined. In optional step 418 the adjustment or the new program parameter can be evaluated for acceptability by a processor against a limit or range of limits in a memory. The limits can be hard coded into the pump or included in a user-customizable drug library that can be downloaded to the processor or memory of the pump over a network. If the adjustment or adjusted program parameter is outside the acceptable range or exceeds an acceptable limit, then an optional alarm is generated in step 420. The alarm can be communicated visually, audibly, by other perceptible means or merely relayed electronically to a remote device. If the adjustment or adjusted program parameter such as a new desired flow rate is within the acceptable range or limit, the method moves back to step 406 and the method continues with the pump processor being automatically programmed to pump the fluid according to the newly adjusted program parameter such as a new flow rate. In other embodiments, one or more steps of the method 400 may be changed in substance or order, one or more steps of the method 400 may not be followed, or one or more additional steps may be added.

Figure 6A:
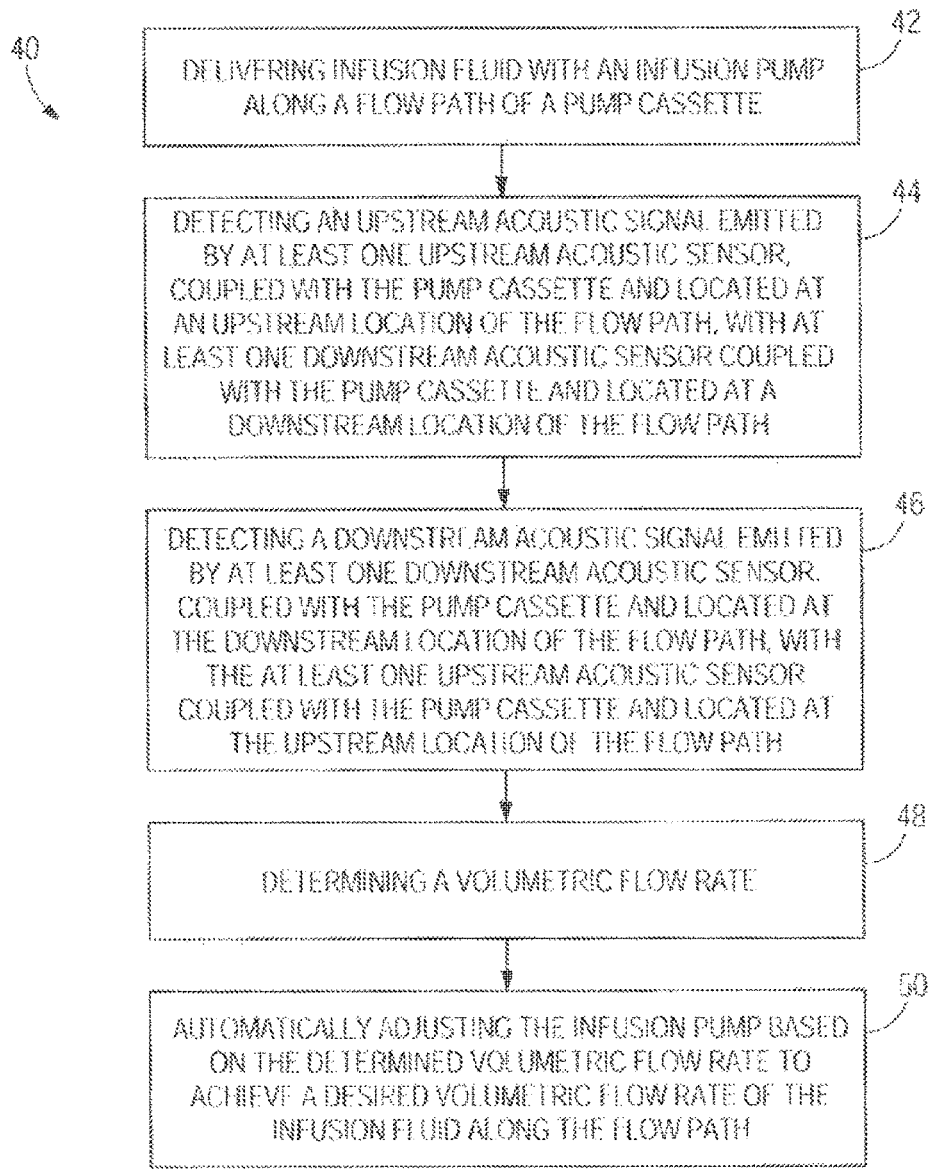
FIG. 6A illustrates another embodiment of a flowchart showing a method of automatically detecting and adjusting a volumetric flow rate delivered by an infusion pump.

With reference to FIG. 6A, in one embodiment the flow measurement step 408 and others from FIG. 6 are disclosed in greater detail as the steps of a flow measurement and automatic adjustment process 40. In step 42, infusion fluid is delivered with an infusion pump along a flow path of a pump cassette. In step 44, an upstream acoustic signal emitted by the upstream acoustic sensor, coupled with the pump cassette and located at an upstream location of the flow path, is detected with the downstream acoustic sensor coupled with the pump cassette and located at a downstream location of the flow path. The upstream acoustic sensor may include at least one ultrasonic upstream acoustic sensor. In other embodiments, the upstream acoustic sensor may vary. In one embodiment, step 44 may include detecting the upstream acoustic signal emitted by the upstream acoustic sensor by receiving the upstream acoustic signal with a first noise cancelling component such as a first noise cancelling microphone.

In step 46, a downstream acoustic signal emitted by the downstream acoustic sensor, coupled with the pump cassette and located at the downstream location of the flow path, is detected with the upstream acoustic sensor coupled with the pump cassette and located at the upstream location of the flow path. The downstream acoustic sensor may include one or more ultrasonic upstream acoustic sensor. In other embodiments, the downstream acoustic sensor may vary. In one embodiment, step 46 may include detecting the downstream acoustic signal emitted by the downstream acoustic sensor by receiving the downstream acoustic signal with a second noise cancelling component such as a second noise cancelling microphone. In step 48, a volumetric flow rate is determined, with the hardware processor, of the infusion fluid along the flow path based on the upstream acoustic signal detected by the downstream acoustic sensor and the downstream acoustic signal detected by the upstream acoustic sensor.

In one embodiment, step 48 may include determining, with the hardware processor, the volumetric flow rate of the infusion fluid along the flow path by determining a first phase delay of the upstream acoustic signal between the upstream acoustic sensor and the downstream acoustic sensor, or by determining a second phase delay of the downstream acoustic signal between the downstream acoustic sensor and the upstream acoustic sensor. This may be done using an algorithm executed by the hardware processor 20.

In another embodiment, step 48 may include determining, with the processor, the volumetric flow rate of the infusion fluid along the flow path by using the algorithm $Q=V*A$, wherein Q includes the volumetric flow rate, V includes a velocity of the infusion fluid generated by the infusion pump, A includes a cross-section area of the flow path, and $V=(L/2)*(1/t_1-1/t_2)$, wherein L includes a length between the upstream location and the downstream location, $t_1$ includes a first time it takes the upstream acoustic signal to travel from the upstream acoustic sensor to the downstream acoustic sensor, and $t_2$ includes a second time it takes the downstream acoustic signal to travel from the downstream acoustic sensor to the upstream acoustic sensor.

In step 50, the infusion pump is automatically adjusted, with the hardware processor, based on the determined volumetric flow rate to achieve a desired volumetric flow rate of the infusion fluid along the flow path. In other embodiments, one or more steps of the method 40 may be changed in substance or order, one or more steps of the method 40 may not be followed, or one or more additional steps may be added. It is noted that the method 40 may utilize any of the system or method embodiments disclosed herein. One or more embodiments of the disclosure allows for improved accuracy of determining how much infusion fluid is being delivered to the patient while decreasing manufacturing cost of the infusion system. It should be understood, of course, that the foregoing relates to exemplary embodiments of the disclosure and that modifications may be made without departing from the scope of the disclosure as set forth in the following claims.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. An infusion system for automatically detecting and adjusting a volumetric flow rate delivered by an infusion pump comprising:
   an infusion pump configured to pump infusion fluid;
   a flow path along which the infusion fluid is configured to be delivered by the infusion pump;
   at least one upstream acoustic sensor located at an upstream location of the flow path;
   at least one downstream acoustic sensor located at a downstream location of the flow path;
   wherein the at least one downstream acoustic sensor is configured to detect an upstream acoustic signal emitted by the at least one upstream acoustic sensor parallel to the flow path, and the at least one upstream acoustic sensor is configured to detect a downstream acoustic signal emitted by the at least one downstream acoustic sensor parallel to the flow path;
   at least one processor in electronic communication with the infusion pump, the at least one upstream acoustic sensor, and the at least one downstream acoustic sensor; and
   at least one memory in electronic communication with the at least one processor, wherein the memory comprises programming code for execution by the at least one processor, and the programming code is configured to determine a volumetric flow rate of the infusion fluid along the flow path based on the upstream acoustic signal detected by the at least one downstream acoustic sensor and on the downstream acoustic signal detected by the at least one upstream acoustic sensor, and to automatically adjust the infusion pump based on the determined volumetric flow rate, to achieve a desired volumetric flow rate of the infusion fluid along the flow path;
   wherein the programming code is configured to determine the volumetric flow rate of the infusion fluid along the flow path based on a first phase delay of the upstream acoustic signal between the at least one upstream acoustic sensor and the at least one downstream acoustic sensor, or on a second phase delay of the downstream acoustic signal between the at least one downstream acoustic sensor and the at least one upstream acoustic sensor.

2. The infusion system of claim 1 wherein the at least one upstream acoustic sensor comprises a first transducer, and the at least one downstream acoustic sensor comprises a second transducer.

3. The infusion system of claim 1 wherein the at least one upstream acoustic sensor comprises a first transmitter and a first receiver, the at least one downstream acoustic sensor comprises a second transmitter and a second receiver, and the first receiver and the second receiver each comprise at least one noise cancelling component.

4. The infusion system of claim 1 wherein the programming code is configured to determine the volumetric flow rate of the infusion fluid along the flow path, over each stroke of the infusion pump, by using an algorithm Q=V*A, wherein Q comprises the volumetric flow rate, V comprises a velocity of the infusion fluid generated by the infusion pump, A comprises a cross-section area of the flow path, and $V=(L/2)*(1/t_1-1/t_2)$, wherein L comprises a length between the upstream location and the downstream location, t1 comprises a first time it takes the at least one upstream acoustic signal to travel from the at least one upstream acoustic sensor to the at least one downstream acoustic sensor, and t2 comprises a second time it takes the at least one downstream acoustic signal to travel from the at least one downstream acoustic sensor to the at least one upstream acoustic sensor.

5. The infusion system of claim 1 wherein the at least one upstream acoustic sensor is located at or integrated with a distal pressure sensor, and the at least one downstream acoustic sensor is located at or integrated with a distal air-in-line air sensor.

6. The infusion system of claim 1 further comprising a pump cassette connected to the infusion pump, wherein the flow path is disposed through the pump cassette, the at least one upstream acoustic sensor is coupled with the pump cassette, and the at least one downstream acoustic sensor is coupled with the pump cassette.

7. The infusion system of claim 1 wherein the programming code is configured to determine, over each stroke of the infusion pump, the volumetric flow rate of the infusion fluid along the flow path based on the upstream acoustic signal detected by the downstream acoustic signal detected by the at least one upstream acoustic sensor and on the at least one downstream acoustic signal detected by the at least one upstream acoustic sensor, to automatically adjust the infusion pump over each pumping cycle of the infusion pump based on the determined volumetric flow rate, to achieve the desired volumetric flow rate of the infusion fluid along the flow path, and to determine, over each stroke of the infusion pump, the volumetric flow rate of the infusion fluid along the flow path based on the first phase delay or on the second phase delay.

8. A method for automatically detecting and adjusting a volumetric flow rate delivered by an infusion pump comprising:
pumping infusion fluid with an infusion pump along a flow path;
detecting an upstream acoustic signal emitted by at least one upstream acoustic sensor parallel to the flow path, located at an upstream location of the flow path, with at least one downstream acoustic sensor located at a downstream location of the flow path;
detecting a at least one downstream acoustic signal emitted by the at least one downstream acoustic sensor parallel to the flow path, located at the downstream location of the flow path, with the at least one upstream acoustic sensor located at the upstream location of the flow path;
determining, with at least one processor, a volumetric flow rate of the infusion fluid, over each stroke of the infusion pump, along the flow path based on the upstream acoustic signal detected by the at least one downstream acoustic sensor and on the at least one downstream acoustic signal detected by the at least one upstream acoustic sensor; wherein the determining, with the at least one processor, the volumetric flow rate of the infusion fluid, over each stroke of the infusion pump, along the flow path comprises determining a first phase delay of the upstream acoustic signal between the at least one upstream acoustic sensor and the at least one downstream acoustic sensor, or determining a second phase delay of the at least one downstream acoustic signal between the at least one downstream acoustic sensor and the at least one upstream acoustic sensor; and
automatically adjusting over each pumping cycle of the infusion pump, with the at least one processor, based on the determined volumetric flow rate, to achieve a desired volumetric flow rate of the infusion fluid along the flow path.

9. The method of claim 8 wherein the detecting the upstream acoustic signal emitted by the at least one upstream acoustic sensor comprises receiving the at least one upstream acoustic signal with a first noise cancelling component, and the detecting the at least one downstream acoustic signal emitted by the at least one downstream acoustic sensor comprises receiving the downstream acoustic signal with a second noise cancelling component.

10. The method of claim 8 wherein the determining, with the at least one processor, the volumetric flow rate of the infusion fluid along the flow path, over each stroke of the infusion pump, comprises determining the volumetric flow rate of the infusion fluid along the flow path, over each stroke of the infusion pump, by using an algorithm $Q=V*A$, wherein Q comprises the volumetric flow rate, V comprises a velocity of the infusion fluid generated by the infusion pump, A comprises a cross-section area of the flow path, and $V=(L/2)*(1/t_1-1/t_2)$, wherein L comprises a length between the upstream location and the downstream location, t1 comprises a first time it takes the upstream acoustic signal to travel from the at least one upstream acoustic sensor to the at least one downstream acoustic sensor, and t2 comprises a second time it takes the at least one downstream acoustic signal to travel from the at least one downstream acoustic sensor to the at least one upstream acoustic sensor.

11. A non-transitory computer readable medium configured to, using at least one processor, automatically detect and adjust a volumetric flow rate delivered by an infusion pump, the non-transitory computer readable medium including programming code to command the at least one processor to:
determine a volumetric flow rate of infusion fluid delivered by an infusion pump, over each stroke of the infusion pump, along a flow path based on: (1) an upstream acoustic signal emitted parallel to the flow path by at least one upstream acoustic sensor, located at an upstream location of the flow path, and detected by at least one downstream acoustic sensor located at a downstream location of the flow path; on (2) a downstream acoustic signal emitted parallel to the flow path by the at least one downstream acoustic sensor and detected by the at least one upstream acoustic sensor; and on (3) a first phase delay of the upstream acoustic signal between the at least one upstream acoustic sensor and the at least one downstream acoustic sensor, or a second phase delay of the downstream acoustic signal between the at least one downstream acoustic sensor and the at least one upstream acoustic sensor; and
automatically adjust the infusion pump over each pumping cycle of the infusion pump, based on the determined volumetric flow rate, to achieve a desired volumetric flow rate of the infusion fluid along the flow path.

12. The non-transitory computer readable medium of claim 11 wherein the programming code is further configured to noise cancel the upstream acoustic signal using the at least one downstream acoustic sensor, and noise cancel the downstream acoustic signal using the at least one upstream acoustic sensor.

13. The non-transitory computer readable medium of claim 11 wherein the programming code is further configured to determine the volumetric flow rate of the infusion fluid along the flow path, over each stroke of the infusion pump, using an algorithm $Q=V*A$, wherein Q comprises the volumetric flow rate, V comprises a velocity of the infusion fluid generated by the infusion pump, A comprises a cross-section area of the flow path, and $V=(L/2)*(1/t_1-1/t_2)$, wherein L comprises a length between the upstream location and the downstream location, t1 comprises a first time it takes the upstream acoustic signal to travel from the at least one upstream acoustic sensor to the at least one downstream acoustic sensor, and t2 comprises a second time it takes the downstream acoustic signal to travel from the at least one downstream acoustic sensor to the at least one upstream acoustic sensor.

* * * * *